US009078585B2

(12) United States Patent
Miyazaki et al.

(10) Patent No.: US 9,078,585 B2
(45) Date of Patent: Jul. 14, 2015

(54) MUSCLE SYNERGY ANALYSIS METHOD, MUSCLE SYNERGY ANALYZER, AND MUSCLE SYNERGY INTERFACE

(75) Inventors: Fumio Miyazaki, Osaka (JP); Hiroaki Hirai, Osaka (JP); Syohei Kawagoe, Osaka (JP); Kazuhiro Matsui, Osaka (JP); Takayuki Nakano, Osaka (JP)

(73) Assignee: Osaka University, Osaka (JP)

( * ) Notice: Subject to any disclaimer, the term of this patent is extended or adjusted under 35 U.S.C. 154(b) by 572 days.

(21) Appl. No.: 13/395,600

(22) PCT Filed: Sep. 8, 2010

(86) PCT No.: PCT/JP2010/065395
§ 371 (c)(1),
(2), (4) Date: Mar. 12, 2012

(87) PCT Pub. No.: WO2011/030781
PCT Pub. Date: Mar. 17, 2011

(65) Prior Publication Data
US 2012/0172745 A1    Jul. 5, 2012

(30) Foreign Application Priority Data

Sep. 14, 2009 (JP) ................. 2009-212149
Feb. 12, 2010 (JP) ................. 2010-029194

(51) Int. Cl.
*A61B 5/04* (2006.01)
*A61B 5/0488* (2006.01)
(Continued)

(52) U.S. Cl.
CPC .......... *A61B 5/0488* (2013.01); *A61B 5/04888* (2013.01); *A61B 5/112* (2013.01); *A61B 5/6828* (2013.01); *A61B 5/7253* (2013.01)

(58) Field of Classification Search
CPC . A61B 5/0488; A61B 5/0492; A61B 5/04882
USPC .......................................... 600/546
See application file for complete search history.

(56) References Cited

U.S. PATENT DOCUMENTS

2006/0073894 A1* 4/2006 Kuramori et al. .......... 463/36
2009/0287374 A1* 11/2009 Kuramori et al. .......... 701/41

FOREIGN PATENT DOCUMENTS

JP  11-192214     7/1999
JP  2007-136041   6/2007
(Continued)

OTHER PUBLICATIONS

Katsumi Yamane, "Contact-Free Estimation of Human Somatosensory Information based on Muscle Tension Ratio Database", 26th Annual Conference of the Robotics Society of Japan Koen Gaiyoshu, The Robotics Society of Japan, Sep. 9, 2008, RSJ2008AC1I3-01.

(Continued)

*Primary Examiner* — Sean Dougherty
*Assistant Examiner* — Daniel Cerioni
(74) *Attorney, Agent, or Firm* — Jordan and Hamburg LLP

(57) ABSTRACT

Disclosed is a muscle synergy analysis which comprises detecting a myoelectric signal generated at each muscle of an antagonistic muscle pair group of a subject; calculating, as time-series data, an antagonistic muscle ratio of an antagonistic muscle pair at a myoelectric signal level from a myoelectric signal detected during a predetermined motion by the subject; and conducting multi variate analysis using the antagonistic muscle ratio at each time of the time-series data as a variable to calculate a principal component including at least a first principal component having high contribution to correlation.

4 Claims, 27 Drawing Sheets

(51) Int. Cl.
  *A61B 5/11* (2006.01)
  *A61B 5/00* (2006.01)

(56) References Cited

FOREIGN PATENT DOCUMENTS

| JP | 2009-212149 | 9/2009 |
|---|---|---|
| WO | WO-2010/013631 | 2/2010 |

OTHER PUBLICATIONS

Akihiko Murai Motion Capture, EMG, Kin no Dotokusei Model ni Motozuku Kinchoryoku no Real Time Suitei Oyobi Kashika, Dai 14 Kai Robotics Symposia Yokoshu, Mar. 16, 2009, pp. 23 to 28.

Kazuhiro Matsui, "EMG Analysis focusing on antagonistic muscle ratio of muscle coordnation", 27th Annual Conference of the Robotics Society of Japan Koen Gaiyoshu, Sep. 15, 2009, RSJ2009AC1P1-08.

Shohei Kawakoshi, "Operating analysis with antagonistic muscle ratio for human upper extremity motion", 27th Annual Conference of the Robotics Society of Japan Koen Gaiyoshu, Sep. 15, 2009, RSJ2009AC1P1-04.

E. Bizzi, V.C.K., Cheung, A,d' Avella, P. Saltiel, M. Tresch, "Combining modules for movement", www.elsevier.com/locate/brainresrev, accepted on Aug. 4, 2007, online received on Sep. 5, 2007.

Robot Motion Control using Surface Electromyogram Signal and Motion Direction Data *Susumu Yamamoto, Masami Tamura, Toru Tsumugiwa, Ryuichi Yokogawa, Doshisha Univ. RSJ2008AC2K2-01, 2 pages, Sep. 9, 2008.

A Human-Exoskeleton Interface Utilizing Electromyography Christian Fleischer and Guenter Hommel p. 872 to 882 IEEE Transactions on Robotics, vol. 24, No. 4, Aug. 2008.

Control method for a Five-Finger EMG-Prosthetic Hand Based on Muscle Synergy Theory Keisuke Shima, Takeshi Takaki, Yusuke Yamada, Toshio Tsuji (Hiroshima University), Akira Otsuka (Prefectural University of Hiroshima) and Takaaki Chin (Hyogo Rehabilitation Center Hospital), 4 pages RSJ2009ACIC1-06 Sep. 15, 2009.

Shared and specific muscle synergies in natural motor behaviors Andrea d'Avella, and Emilio Bizzi pp. 3076 to 3081 Feb. 22, 2005, vol. 102, No. 8.

* cited by examiner

[Examined muscle]

[The scores of components of muscles coordination of muscle contraction]

4.0 [km/h]

3.0 [km/h]

[The components of muscles coordination of muscle contraction]

[The activity calculated by antagonistic muscles]

ACTUAL MOTION

IDEAL (REFERENCE)

DIFFERENCE

[ Exponential set up ]

[ Joint angles ]

[ Component ]

[ Process of the relationship between P1 and P2 ]

MUSCLE SYNERGY ANALYSIS METHOD, MUSCLE SYNERGY ANALYZER, AND MUSCLE SYNERGY INTERFACE

TECHNICAL FIELD

The present invention relates to muscle synergy related techniques for a muscle pair group moving based on myoelectric signals.

BACKGROUND OF THE INVENTION

Effective training in sports activity, for example, needs a trainer who can correctly evaluate a body motion as a target. The number of such trainers is not enough than the sports population, and the evaluation depends on experiences or the like and is not necessarily constant. Meanwhile, attempts have been made for quantitative evaluation of a target motion from an engineering standpoint. Many of such attempts, however, are just superficial evaluation based on the performance of the overall motion or information from a sensor attached on a body surface.

Recently a system is described to estimate and visualize in real time the muscle action inside a human body during general motions (Non Patent Literature 1). This system includes a motion capture system detecting markers attached to a subject, a floor reaction force indicator including a plate-form pressure-sensing device to detect the motion of the subject and a computer that executes a given operation to the detected results. Such a system attracts much attention for the specific analysis ability of a body motion and its potential applicability to deep sense estimation. This system enables visualization of muscle tension during general motions mainly on the basis of kinesiological data.

Patent Literature 1 describes a technique of detecting a tension of each of a plurality of muscles based on myoelectric signals of the muscles measured using an electromyograph, and generating a machine learning model to estimate a time-series combination of a plurality of joint states on the basis of a history of a plurality of joint states decided from a tension of each muscle and tension of a plurality of muscles. According to this technique, the muscle motion is not limited, and a desired plurality of joint states and a time-series combination of these states can be precisely and quickly estimated on the basis of myoelectric signals of a plurality of muscles.

Non Patent Literature 2 describes the combination of muscle synergies for motion. More particularly, Non Patent Literature 2 discloses a method of converting time-series myoelectric signals each detected from thirteen muscles into a synthetic variable (score) represented by five types of main components by multivariate analysis. In this way, the number of types of variables in a control target model is reduced, whereby motion understanding and mechanical control for a model can be facilitated.

CITATION LIST

Patent Literature

Patent Literature 1: Japanese Patent Application Laid-Open No. 2007-136041

Non Patent Literatures

Non Patent Literature 1: Akihiko MURAI, Kosuke KUROSAKI, Katsu YAMANE, and Yoshihiko NAKAMURA, "Realtime Estimation and Visualization of Muscle Tension Based on Motion Capture, EMG, and Dynamic Muscle Model" Proceedings of the 14th Robotics Symposia, Hokkaido, Japan, Mar. 16, 2009 (in Japanese).

Non Patent Literature 2: E. Bizzi, V. C. K, Cheung, A. d'Avella, P. Saltiel, M. Tresch, "Combining modules for movement", www.elsevier.com/locate/brainresrev, accepted on Aug. 4, 2007, online received on Sep. 5, 2007

SUMMARY OF THE INVENTION

Non Patent Literature 1, however, has the problems of becoming large in scale and high cost because the system requires a motion capture system and a floor reaction force indicator. Further, since the system is targeted at general motions for analysis, enormous flexibility has to be dealt with, and so computational cost cannot be ignored to achieve real-time computation. Further, a body model has to be identified for each subject person, thus requiring an adequate body musculoskeletal model therefor. Patent Literature 1 requires a three-dimensional position measurement device at the stage of learning by a machine, thus becoming large in scale. These Non Patent Literature 1 and Patent Literature 1 do not describe multivariate analysis (principal component analysis) conducted to a plurality of variables.

On the other hand, Non Patent Literature 2 describes the approach of reducing the number of variables (i.e., compressing a motion pattern) by multivariate analysis conducted to a large number of myoelectric signals. In Non Patent Literature 2, however, analysis is just made to time-series myoelectric signals, and the concept related to muscle coordination resulting from a specific motion, i.e., task-oriented type muscle coordination is not included. Accordingly, cost and time necessary for computation cannot be ignored.

The present inventors has proposed a muscle synergy analysis method and an apparatus therefor enabling motion evaluation using fewer types of principal components by obtaining muscle synergy specific to muscle coordination in a predetermined motion such as upper limb rotation or walking by a subject such as a human and conducting multivariate analysis thereto (Japanese Patent Application No. 2009-212149). More specifically, this muscle synergy analysis method includes the steps of: detecting a myoelectric signal generated at each muscle of an antagonistic muscle pair group of a subject; calculating, as time-series data, an antagonistic muscle ratio of an antagonistic muscle pair at a myoelectric signal level from the myoelectric signal detected during a predetermined motion by the subject; and conducting multivariate analysis using the antagonistic muscle ratio at each time of the time series data as a variable to calculate first and second principal component scores, for example, having high contribution to correlation. This method enables evaluation of a motion with fewer types of principal components.

As in the above proposal, the present inventors found high contribution degree of correlation existing between a myoelectric signal generated at an antagonistic muscle pair and a principal component scores. However, mechanism between a motion command from the motor area of a cerebrum and a myoelectric potential command to an antagonistic muscle pair is still not understood, and such finding is not enough for a control system.

It is an object of the present invention to provide a muscle synergy analysis method and an apparatus therefor, by which muscle synergy in a muscle coordination relationship specific to a predetermined motion by a subject is obtained, and multivariate analysis is conducted thereto so as to enable motion evaluation using fewer types of principal components.

It is another object of the present invention to provide a muscle synergy interface based on muscle synergy, capable of creating an action command for each of a large number of muscles from fewer motion commands.

A muscle synergy analysis method according to the present invention includes the steps of: detecting a myoelectric signal generated at each muscle of an antagonistic muscle pair group of a subject; calculating, as time-series data, an antagonistic muscle ratio of an antagonistic muscle pair at a myoelectric signal level from a myoelectric signal detected during a predetermined motion by the subject; and conducting multivariate analysis using the antagonistic muscle ratio at each time of the time-series data as a variable to calculate a principal component including at least a first principal component having high contribution to correlation.

A muscle synergy analyzer according to the present invention includes: a detector that detects a myoelectric signal generated at each muscle of an antagonistic muscle pair group of a subject; antagonistic muscle ratio calculation means that calculates, as time-series data, an antagonistic muscle ratio of an antagonistic muscle pair at a myoelectric signal level from a myoelectric signal detected by the detector during a predetermined motion by the subject; and first principal component analysis means that conducts multivariate analysis using the antagonistic muscle ratio at each time of the time-series data as a variable to calculate a principal component including at least a first principal component having high contribution to correlation. Herein, the time-series data may be a normalized ratio of an antagonistic muscle pair at a myoelectric signal level, i.e., a normalized antagonistic muscle ratio.

According to these aspects of the present invention, a myoelectric signal generated at each muscle of an antagonistic muscle pair group of a body part as an examination target that is a subject such as a human can be detected during a predetermined motion by a detector in a time-series direction. Next, the first principal component analysis means conducts multivariate analysis using the antagonistic muscle ratio at each time of the time-series data as a variable to calculate a principal component including at least a first principal component having high contribution to correlation. Therefore, the apparatus can be made compact than conventional ones.

In this way, instead of conducting a multivariate analysis (in this case a principal component analysis) to a myoelectric potential matrix of the muscles, the idea of an antagonistic muscle ratio is introduced with consideration given to muscle coordination in the motion, and then a principal component analysis is conducted to this idea. Thereby the types of variables in number can be reduced, thus facilitating and speeding up the processing and so enabling real-time processing. Further, complicated and difficult processing of identifying parameters of various parts of a body is not required, and accordingly the processing can be simplified. When the types of variables after the principal component analysis is up to the third principal component, display can be advantageously performed in a three-dimensional coordinate system. Further, the use of antagonistic muscle ratios allows a different principal component analysis result to be obtained for each type of the motion, and therefore the number and scores of principal components suitable for a motion can be obtained.

The thus calculated principal component scores are processed as needed. For instance, when outputting the principal component scores simply (typically displaying on a monitor), in applicable embodiments, they may be output for a compassion with other persons, they may be output for a comparison with an ideal motion (reference information) of the same person, or a difference between information on ones' ideal motion and a measurement result this time may be calculated and the calculated difference may be displayed for a comparison with the ideal motion of the same person. Especially in the embodiments for a comparison with his/her own information, a task-oriented type can be implemented in terms of a comparison with ideal one for a specific motion. Further, the present invention can be used to analyze skillfulness in an expert's motion, and so can be useful in the fields of sports science and kinesiology.

A muscle synergy interface according to the present invention is configured to let a plurality of muscles perform a predetermined motion. The muscle synergy interface includes: motion command setting means that inputs motion information to specify a motion to be performed by the plurality of antagonistic muscle pair groups; first conversion means that converts the motion information into a principal component information; and second conversion means that converts the principal component information into a potential signal to be applied to each antagonistic muscle pair.

According to this aspect of the present invention, when the motion command setting means inputs motion information to specify a motion to be performed by the plurality of antagonistic muscle pair groups, the first conversion means converts the motion information into a principal component information, and next the second conversion means converts the principal component information into a potential signal to be applied to each antagonistic muscle pair. Then, each antagonistic muscle pair is made to perform muscle action in accordance with each corresponding potential signal obtained by the conversion, whereby a specified motion is executed. Therefore, a motion instruction to each antagonistic muscle pair can be issued with less principal component information having high correlation. As a result, the processing can be speeded up and the configuration can be made more compact than conventional ones.

According to the present invention, muscle synergy in a muscle coordination relationship specific to a predetermined motion by a subject can be obtained, and a multivariate analysis conducted enables motion evaluation using fewer types of principal components.

According to the present invention, a motion instruction to each antagonistic muscle pair can be issued with less principal component information having high correlation. As a result, the processing can be speeded up and the configuration can be made more compact than conventional ones.

BRIEF DESCRIPTION OF THE DRAWINGS

FIG. 25A illustrates Experiments 1 and 2 and FIG. 25B illustrates Experiment 3.

FIG. 26A is a diagram of a breakdown of walking (3 km/h) and FIGS. 26B, 26C illustrate principal components w1 and w2 at that time.

FIG. 27A is a diagram of a breakdown of walking (3 km/h), FIG. 27B illustrates information on the principal component w1 at that time and FIG. 27C illustrates information on the principal component w2 at that time.

DESCRIPTION OF THE PREFERRED EMBODIMENTS

Figure 1:
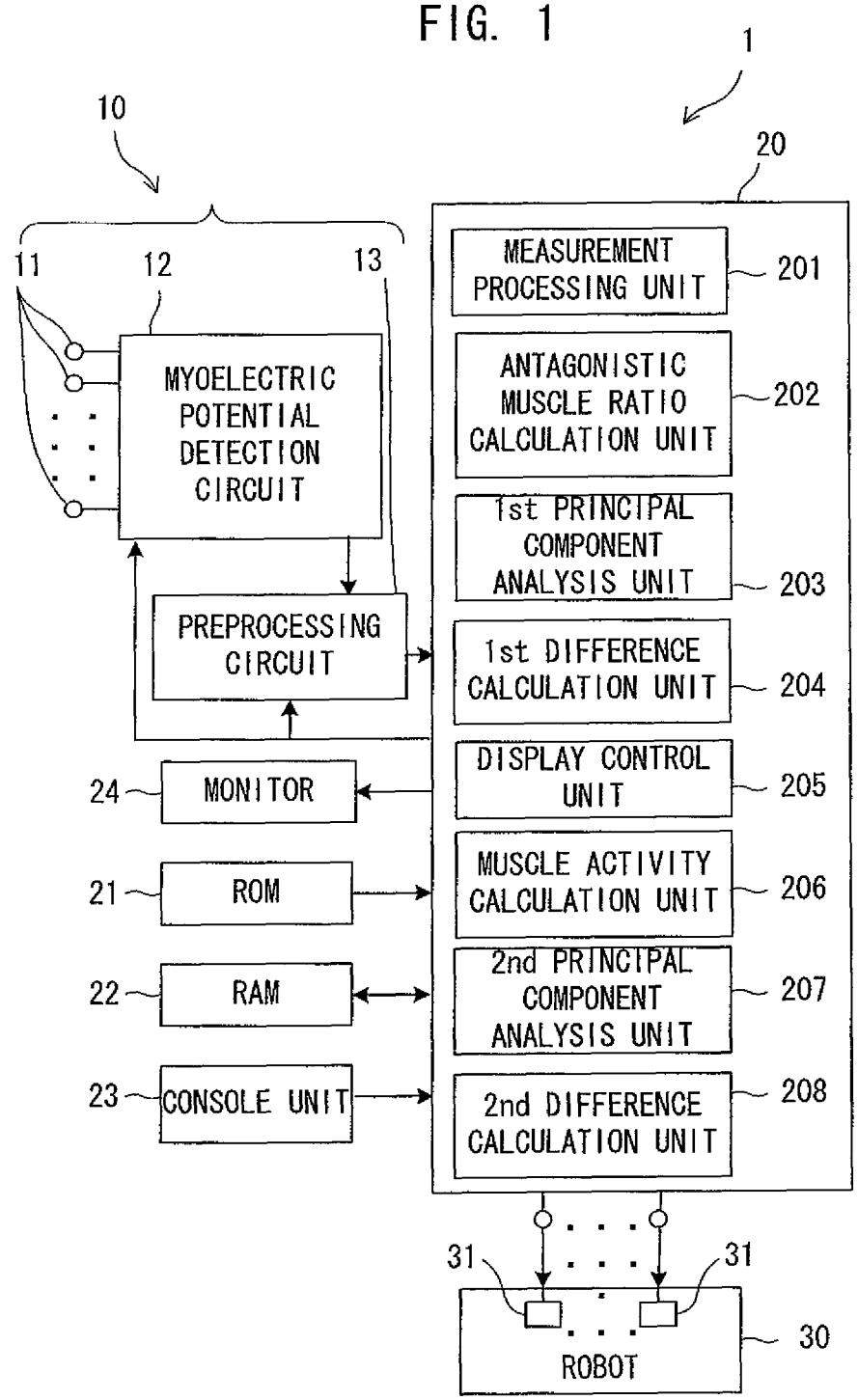
FIG. 1 illustrates the overall configuration of a muscle synergy analyzer that is one embodiment of the present invention.

FIG. 1 illustrates the overall configuration of a muscle synergy analyzer that is one embodiment of the present invention. This apparatus 1 includes an electromyograph 10 to detect a myoelectric potential of a subject and a signal processing unit 20 including a microcomputer or the like to perform predetermined signal processing on the basis of the detected myoelectric potential. To this apparatus 1 is connected a robot 30 as needed by wired via a terminal or by wireless connections. The robot 30 includes a plurality of actuators 31 to move a mechanical body at a required part. The actuators 31 may be configured with McKibben-type artificial muscles, for example, capable of controlling a pneumatic pressure in accordance with an electrical signal to expand or contract a pneumatic rubber tube. The actuators 31 receive a signal from the signal processing unit 20 as a driving signal for operation. The actuators 31 are not limited to McKibben-type artificial muscles, and may be an electro-mechanical converter such as an electromagnetic solenoid, a piezoelectric device or a motor that generates a mechanical motion from an electrical signal or using another force obtained by converting an electrical signal.

The electromyograph 10 includes a required number of electrodes 11, an myoelectric potential detection circuit 12 that detects an electric signal generated at each electrode 11, and a preprocessing circuit 13 that performs predetermined preprocessing to a detected electric signal. The electrodes 11 are made of a conductive material and have a predetermined shape such as a circle shape with a diameter of a few to dozens millimeters preferably, and with a diameter of about 10 mm in the present embodiment. The myoelectric potential detection circuit 12 has a required number of connection terminals to be connected to the corresponding electrodes 11 via leads or wirelessly. The myoelectric potential detection circuit 12 repeatedly fetches myoelectric potentials input to the terminals one by one and in a time-division manner. The myoelectric potential detection circuit 12 may fetch signals in a synchronization manner. The myoelectric potential signals are AC signals at the level of a few $\mu V$ to a few mV with the frequency of about a few Hz to dozens KHz. Therefore, the preprocessing circuit 13 is provided with an amplifier to amplify the myoelectric potential signals to a processable level (a few V), a band-pass filter to let a signal with a frequency of 10 Hz to 150 Hz that is a major frequency band of the myoelectric potential pass therethrough and a full-wave rectifier. The preprocessing circuit 13 is further provided with an AD converter at an output side so as to enable digital processing of the myoelectric potential signals. A part of the preprocessing circuit 13, e.g., a filter thereof may be a digital filter that is software implemented in the signal processing unit 20.

The signal processing unit 20 is configured with a microcomputer having a CPU, to which a ROM 21 to store a processing program for signal processing according to the present invention and required image information, a RAM 22 to store data being processed temporarily, a console unit 23 including a ten key, a mouse or the like to accept required instructions and a monitor 24 are connected. The monitor 24 displays input information input from the console unit 23 for checking and processing results. The processing program in the ROM 21 is read out to the RAM 22 and is executed while being held.

The CPU of the signal processing unit 20 executes the processing program held on the RAM 22, thus functioning as a measurement processing unit 201 to execute measurement processing of myoelectric potentials, an antagonistic muscle ratio calculation unit 202 to calculate an antagonistic muscle ratio for a predetermined antagonistic muscle pair from the fetched myoelectric potentials, a first principal component analysis unit 203 to execute multivariate analysis (principal component analysis) to the calculated antagonistic muscle ratio to set principal components and calculate their scores, a first difference calculation unit 204 to calculate a difference between a reference principal component score that is fetched beforehand as a reference and a principal component score obtained from a new measurement, both of the scores being calculated by the first principal component analysis unit 203, and a display control unit 205 to display a difference from the reference principal component score on the monitor 24 as well as a result of the principal component analysis on the monitor 24.

The CPU of the signal processing unit 20 executes the processing program held on the RAM 22, thus further functioning as a muscle activity calculation unit 206 to calculate a muscle activity for a predetermined antagonistic muscle pair from the fetched myoelectric potential, a second principal component analysis unit 207 to execute multivariate analysis (principal component analysis) to the calculated muscle activity to set principal components and calculate their scores, and a second difference calculation unit 208 to calculate a difference between a reference principal component score that is fetched beforehand as a reference and a principal component score obtained from a new measurement, both of the scores being calculated by the second principal component analysis unit 207.

The display control unit 205 functions as first display control means to display a difference calculated by the first difference calculation unit 204 on the monitor 24 and as second display control means to display a difference calculated by the second difference calculation unit 208 on the monitor 24.

The first and second first principal component analysis units 203 and 207 further calculate contribution of the respective principal components, and a first principal component, a second principal component . . . in the descending order of contribution are used until their cumulative contribution (cumulative value) exceeds a predetermined threshold, e.g., 90%.

Prior to the measurement, an agent for reducing skin resistance is applied to a part of a subject performing a predetermined motion (a specific task, i.e., of a task-oriented type), i.e., at a skin surface of a muscle on a surface side as a measurement target, and the electrode 11 is attached thereon. In this state, the subject performs the predetermined motion, e.g., walking.

Figure 2:
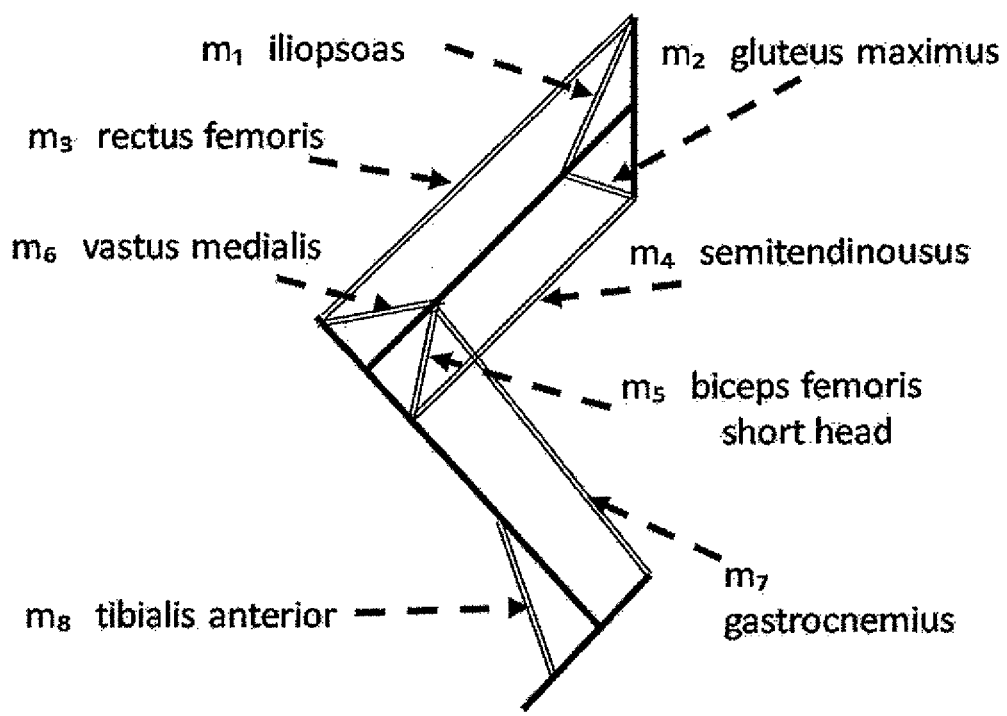
FIG. 2 schematically illustrates names and attached positions of eight muscles of a right lower leg involved in a walking motion as an example of the muscles of a subject.

FIG. 2 schematically illustrates the names and attached positions of eight muscles of a right lower leg involved in the walking motion as an example of the muscles of a subject. FIG. 2 illustrates flexors and extensors of hip joint mono-articular muscles, hip joint/knee joint bi-articular muscles, knee joint mono-articular muscles and ankle joint muscles that are eight muscles in total from m1 to m8. Table 1 illustrates the eight muscles in pairs of flexors and extensors.

TABLE 1

Antagonistic muscle ratio

| Ratio NO. | Pair | Function |
|---|---|---|
| $r_1$ | $m_2/m_1$ | Hip extention |
| $r_2$ | $m_3/m_4$ | Knee extention • Hip flexion |
| $r_3$ | $m_6/m_5$ | Knee extention |
| $r_4$ | $m_7/m_8$ | Ankle extention |
| $r_5$ | $m_2/m_3$ | Hip extention |
| $r_6$ | $m_3/m_5$ | Knee extention (Hip flexion) |
| $r_7$ | $m_1/m_4$ | Hip flexion |
| $r_8$ | $m_4/m_6$ | Knee flexion (Hip extention) |

Ratios r1 to r8 of Table 1 represent the number of antagonistic muscle ratios. Among them, r1 to r4 are ratios of antagonistic muscle pair groups relating to mono-articular muscles, and r5 to r8 are ratios of antagonistic muscle pair groups including bi-articular muscles. Table 1 is based on the report on an action by coordination of bi-articular muscles and mono-articular muscles in a bi-articular structure ("Humanoid Kogaku, seibutsu shinka kara manabu, nikansetsu robotto kikou" (in Japanese) or "Revolution in humanoid robotics: evolution of motion control" written and edited by Minayori KUMAMOTO, Tokyo, Japan, 2006). Note here that other tables different from Table 1 are prepared for the motions using an arm and a hand, for example (see Tables 2 and 3, details described later).

The measurement processing unit 201 is configured to detect a myoelectric potential over time from each electrode 11 in response to a motion by a subject. For instance, a series of a motion is divided into a plurality of segments, and an average of myoelectric potentials in the segments is found, for example, to decide a myoelectric potential for each segment. The myoelectric potential is represented as percentage with respect to the maximum detected potential for each measured muscle (% Maximum Voluntary Contraction: % MVC) and output. A predetermined motion may be performed a plurality of times consecutively, and an average of detected data for the predetermined motion may be found to improve detection accuracy.

Herein, let that t denotes a time for each segment and $m_{pt}$ denotes the value of % MVC of each muscle p in each segment, then a muscle active data matrix M can be represent by Expression 1, including the values of % MVC for each time of each muscle in rows arranged in the order of muscles.

[Expression 1]

$$M = \begin{pmatrix} m_{11} & \cdots & m_{1t} \\ \vdots & \ddots & \vdots \\ m_{p1} & \cdots & m_{pt} \end{pmatrix} \quad (1)$$

Let that t denotes a time for each segment and $r_{tp}$ denotes the value of an antagonistic muscle ratio calculated for each antagonistic muscle ratio number p in each segment, then a matrix R can be represented by Expression 2, including antagonistic muscle ratios of eight muscles for each time in the rows that are arranged vertically in the time-series order. The antagonistic muscle ratio calculation unit 202 calculates numerical values of each row and column.

[Expression 2]

$$R = \begin{pmatrix} r_{11} & \ldots & r_{1p} \\ \ldots & \ldots & \ldots \\ r_{t1} & \ldots & r_{tp} \end{pmatrix} \quad (2)$$

Subsequently, the first principal component analysis unit 203 performs a principal component analysis to the matrix R. As a result, an average value $E_r$ of the antagonistic muscle ratios can be found as in Expression 3.

[Expression 3]

$$\overline{E}_r = \{\overline{r}_1, \ldots, \overline{r}_n\} \quad (3)$$

The matrix R is to find muscle coordination by a principal component analysis. The muscle activity calculation unit 206 adds the values of % MVC of an antagonistic muscle pair in Expression 1. The added value is referred to as muscle activity. On the basis of an idea similar to the above, the second principal component analysis unit 207 performs a principal component analysis to the muscle activity as well. Preferably the muscle activity calculation unit 206 performs calculation using the same pair as the antagonistic muscle pair used by the antagonistic muscle ratio calculation unit 202, which is not a limiting example. The first and second principal component analysis units 203 and 207 can reduce, i.e., compress, parameters in number corresponding to the number of muscles into the number of types of principal components, and accordingly the processing load in the following process can be reduced and prompt processing is enabled.

Among the principal components calculated by the principal component analysis, n pieces of principal components having high contribution are decided. Among these principal components, the component having the k-th highest contribution is called a k-th principal component, and an eigenvalue $\lambda_k$ for the k-th principal component is found as in Expression 4, and a corresponding contribution $c_k$ and a cumulative contribution $C_k$ are represented as in Expressions 5 and 6.

[Expression 4]

$$\lambda = \{\lambda_1, \ldots, \lambda_k, \ldots, \lambda_n\} \quad (4)$$

[Expression 5]

$$c = \{c_1, \ldots, c_k, \ldots, c_n\} \quad (5)$$

[Expression 6]

$$C = \{C_1, \ldots, C_k, \ldots, C_n\} \quad (6)$$

The first and second difference calculation units 204 and 208 calculate a difference between a reference principal component score as a reference that is fetched beforehand and a principal component score obtained by a new measurement.

Figure 3:
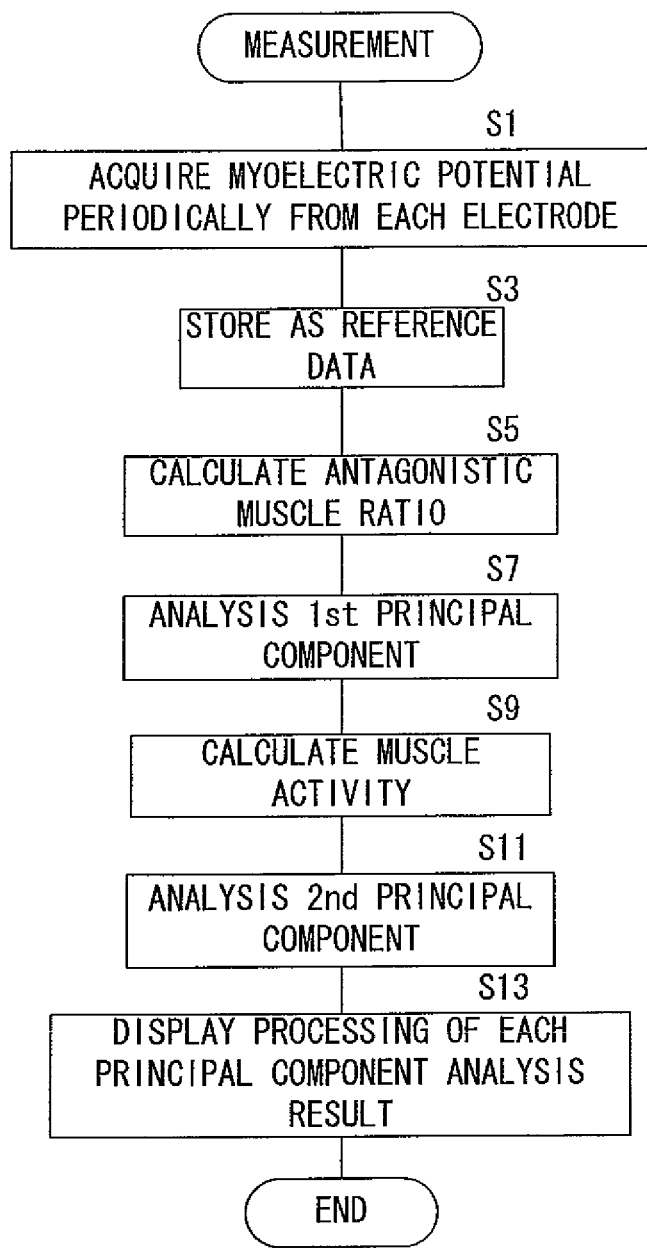
FIG. 3 is a flowchart illustrating exemplary measurement processing executed by a signal processing unit.

Next, FIG. 3 is a flowchart illustrating exemplary measurement processing executed by the signal processing unit 20. This flowchart is to acquire reference information as a reference of a subject. Firstly prior to the processing (or at the end of the processing), information to identify a subject, e.g., a name of the subject is registered.

Thereafter, myoelectric potentials are acquired periodically from the electrodes 11 via the preprocessing circuit 13 (Step S1), and the acquired myoelectric potential data is stored in the RAM 22, for example (Step S3). Next, an antagonistic muscle ratio is calculated (Step S5), and first principal component analysis is conducted to the calculated antagonistic muscle ratio (Step S7).

Subsequently, muscle activity is calculated on the basis of reference data (Step S9), and second principal component analysis is conducted to the calculated muscle activity (Step S11). Next, results of the principal component analyses are displayed for checking on the monitor 24 (Step S13). About an image on the monitor 24, processing is finished without input with a abnormality from the console unit 23, measurement for reference data acquisition is finished. If the image shows abnormality of the measurement result, measurement may be performed again in a similar manner. In the present embodiment, while myoelectric potential data is stored, the first and second principal component analyses are just displayed for checking and data thereof are not stored. The results of the first and second principal component analyses may be stored beforehand, and in such an embodiment storing the results beforehand, calculation is not required for each difference display in the following processing.

Figure 4:
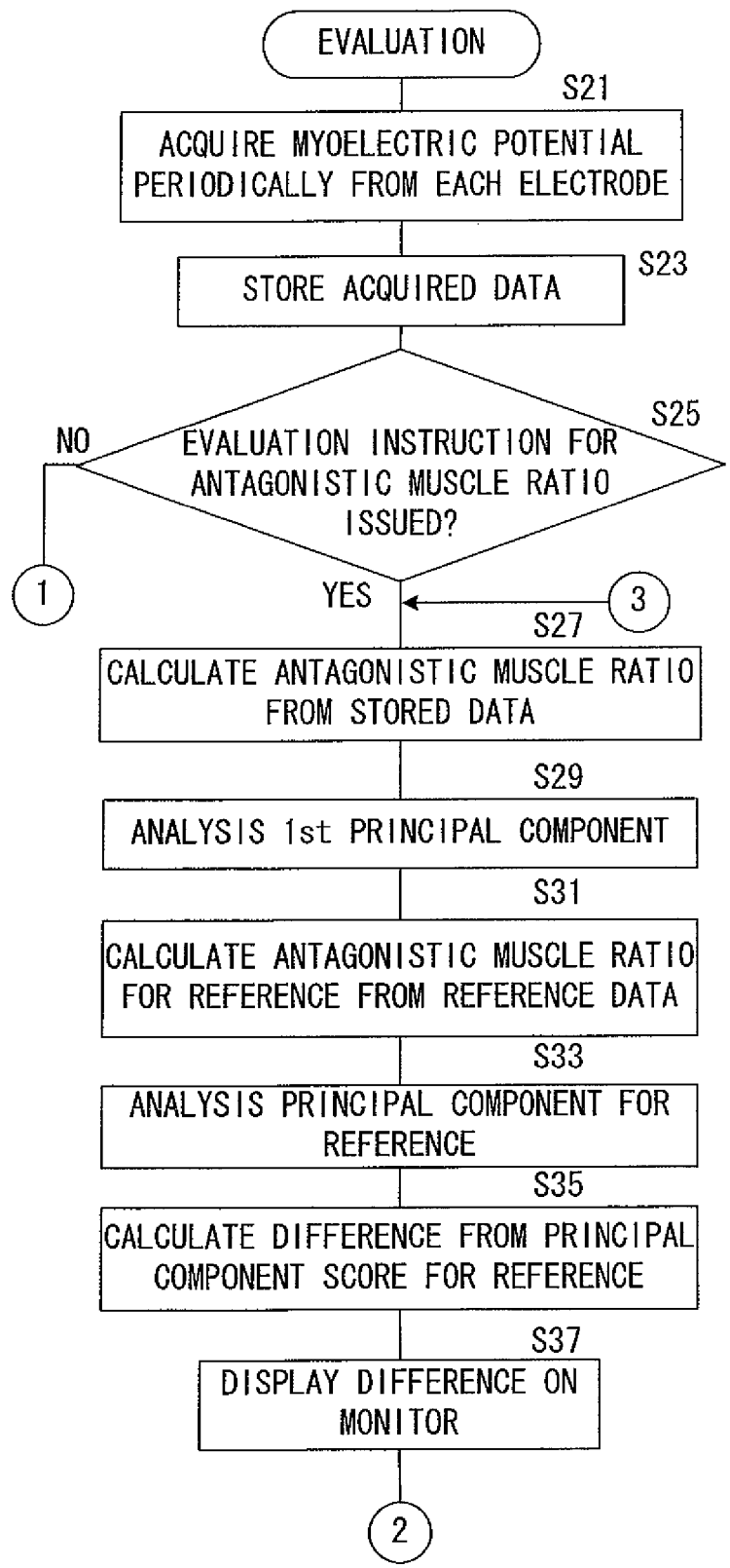
FIG. 4 is a flowchart illustrating exemplary evaluation processing executed by a signal processing unit.
Figure 5:
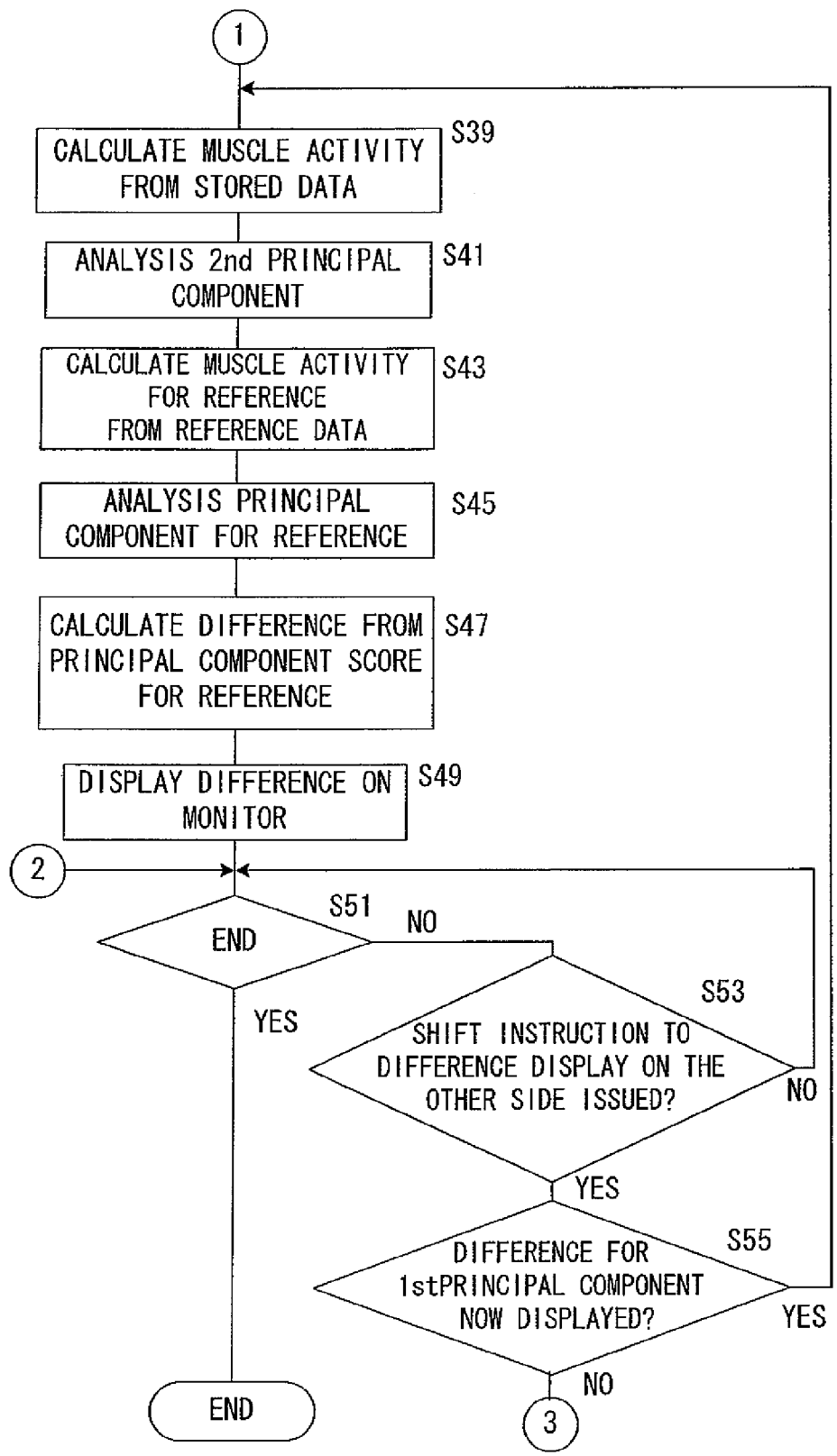
FIG. 5 is a flowchart illustrating exemplary evaluation processing executed by a signal processing unit.

FIGS. 4 and 5 are flowcharts illustrating exemplary evaluation processing executed by the signal processing unit 20. In general this flowchart is to be performed to the same subject as in FIG. 3. That is, prior to the evaluation, the name of a subject as an evaluation target is input, and the input name is checked against already registered names, and if there is a corresponding name, the procedure shifts to Step S21. On the other hand, if there is no corresponding name, the subject is regarded as a not-registered subject and preferably the flowchart of FIG. 3 is executed.

Next, myoelectric potentials are acquired periodically from the electrodes 11 via the preprocessing circuit 13 (Step S21), and the acquired myoelectric potential data is stored in the RAM 22 (Step S23). Next, determination is made as to whether an evaluation instruction for antagonistic muscle ratio is issued or not (Step S25). When this determination is YES, an antagonistic muscle ratio is calculated on the basis of stored data (Step S27), and subsequently first principal component analysis is executed to find a principal component score (Step S29).

Subsequently, reference myoelectric potential data is read out, which is stored for the same subject, and an antagonistic muscle ratio for reference is calculated (Step S31), and first principal component analysis for reference is executed (Step S33).

Subsequently, a difference between the principal component score obtained at Step S29 and the principal component score obtained at Step S33 is calculated (Step S35), and a result thereof is displayed on the monitor 24 (Step S37). Since there are a plurality of types of principal components as in the first principal component, the second principal component, . . . , they are displayed as rectangular coordinate axes on the monitor 24. Calculation of a difference of both principal component scores may be performed in the units of coordinate axes, and a result thereof may be displayed on the monitor 24 in a single element manner, or calculation may be collectively for a difference of a plurality of elements, and a result thereof may be displayed.

During displaying of the difference on the monitor 24, determination is made as to whether display is to be finished, e.g., whether a termination key is pressed or not (Step S51). When the display is not to be finished, the procedure proceeds to Step S53.

On the other hand, when the determination is NO at Step S25, muscle activity is calculated on the basis of stored data (Step S39), and subsequently second principal component analysis is executed to find a principal component score (Step S41). Subsequently reference myoelectric potential data stored for the same subject is read out, muscle activity for reference is calculated (Step S43) and second principal component analysis for reference is executed (Step S45).

Subsequently, a difference between the principal component score obtained at Step S41 and the principal component score obtained at Step S45 is calculated (Step S47), and a result thereof is displayed on the monitor 24 (Step S49). The way of the display is substantially similar to Step S37.

Then, at Step S51, determination is made as to whether the procedure is to be finished or not, and when the procedure is to be finished, e.g., when a termination key, for example, is pressed, the flow is exited. On the other hand, when the procedure is not to be finished, at Step S53, determination is made as to whether an instruction to shift to difference display on the other side is issued or not. For instance, a specific key may be assigned for this instruction, for example. When there is no instruction issued to shift to difference display on the other side, the procedure proceeds to Step S51. On the other hand, when an instruction is issued to shift to difference display on the other side, determination is made as to whether difference display of a score by the first principal component analysis is currently performed or not (Step S55). When this determination is YES, the procedure is switched to the calculation of a score by second principal component analysis and a difference display state therefor (shift to Step S39). When the determination is NO, the procedure is switched to the calculation of a score by first principal component analysis and a difference display state therefor (shift to Step S279). Herein, when calculation for the principal component analysis and difference display are performed, and data thereof is stored temporarily, whereby determination is made that such calculation for the principal component analysis and difference display are performed, then, after Step S55, switching is performed to a difference display state of a score by the second principal component analysis (shift to Step S49). When the determination is NO, switching is performed to a difference display state of a score by the first principal component analysis (shift to Step S37).

According to such a configuration and processing, the apparatus includes an electromyograph 10 and a signal processing unit 20 including a computer, and therefore a compact and low-cost apparatus can be provided, thus facilitating a widespread use thereof.

Further, a difference between a principal component score and a reference principal component score based on principal component analysis for antagonistic muscle ratio or a difference between a principal component score and a reference principal component score based on principal component analysis for muscle activity is displayed, whereby quantitative evaluation is enabled, and so the way of modifying muscle synergy necessary for a more ideal motion (how to move a body) can be shown. Moreover, a difference result is used as evaluation information, which can be applied to a robot system capable of directly showing a motion to a user or a functional electric stimulation system. As a result, the apparatus is applicable to a new way of coaching or rehabilitation.

The following describes examples of experiments.

Example Experiment 1

EMG (electromyogram to directly measure muscle action) measurement was performed for a walking motion by a healthy male person as a subject. Muscle coordination was emphasized and the concept of a ratio of antagonistic muscles to be considered a minimal unit of the muscle coordination was introduced, and principal component analysis was conducted using the concept. Thereby, antagonistic muscle ratios of eight muscles were able to be compressed into three patterns. Further, the concept of muscle activity to add actions of antagonistic muscles was introduced, and considering the muscle activity as well as the antagonistic muscle ratio used, the following describes that functions of an antagonistic muscle group plays a very important role for muscle coordination.

Experiment Method

In the present research, focusing on the muscle action during walking on a treadmill, eight muscles of the right lower limb of a healthy male person (23 years old, 174.5 cm in height, 48 kg in weight, right-footed) walking at a natural speed were selected and myoelectric potentials thereof were measured (see FIG. 2).

Experiment Equipment

Myoelectric potentials were measured using surface electrodes of 10 mm in size with the interelectrode distance set at 20 mm. The myoelectric potentials were amplified with a myoelectric potential acquisition device and a bio-amplifier WEB-9000 (produced by Nihon Kohden), and thereafter using an AD converter/recorder LX-110 (produced by TEAC) and an image recorder AQVU (produced by TEAC), a camera image was recorded in a synchronized manner. The camera image data was used for judging a gait phase. The gait phase includes one gait cycle from right-heel contact with the ground to next right-heel contact with the ground, and includes a double stance phase when both legs are in contact with the ground, a single stance phase when a right lower leg only is in contact with the ground and a swing phase when the right lower leg is not in contact with the ground. The one gait cycle is divided into the double stance phase, the single stance phase, the double stance phase and the swing phase in this stated order. The sampling frequency was 1 KHz.

(Examined Muscles)

Based on the aforementioned report on the action by corporation of bi-articular muscles and mono-articular muscles in a bi-articular structure (written and edited by Minayori KUMAMOTO, as stated above), eight muscles in pairs of flexors and extensors for hip joint mono-articular muscles, hip joint/knee joint bi-articular muscles, knee joint mono-articular muscles and ankle joint muscles were targeted. FIG. 2 illustrates the name of the muscles and their attached positions.

(Experiment Environment)

Before attaching the electrodes 11 to a subject (examinee), the skin was treated with SkinPure (produced by Nihon Kohden) to lower skin resistance to 10 kΩ or less. The subject walked on a treadmill T650m (produced by SportsArt Fitness) at speeds of 3.0 km/h and 4.0 km/h each for one minute, and myoelectric potentials at these speeds were measured during walking.

(Data Processing)

As stated above, for normalization among the muscles, the myoelectric potentials are represented by percentage % MVC with reference to the myoelectric potential at the maximum isometric contraction. To this end, the myoelectric potential during the maximum isometric contraction was measured beforehand for each muscle. Actually measured values and data for normalization underwent rectification, filtering (10 to 150 Hz band-pass) and smoothing, and the actually measured values were divided by the data for normalization to represent data by percentage. Thereafter, data was averaged for each gait cycle, and the time axis also was represented by percentage (1000 points). Further, data was averaged for 5(%) time period and the time was represented as (t1 ... t20). Among the muscles, muscles acting antagonistic to each other were paired as a muscle pair group, and the mutual ratio was calculated as an antagonistic muscle ratio. In this experiment, the antagonistic muscle ratios paired as in Table 1 were used.

(Analysis)

The obtained data contained information on the eight muscles, and in order to represent such information with fewer parameters, principal component analysis was conducted to the data. As a result, flexibility of the eight muscles could be compressed into less number of elements, and such compressed information could lead to muscle coordination. Letting that p denotes the antagonistic muscle ratio No., t denotes each time duration and $r_{tp}$ denotes each antagonistic muscle ratio, Expressions 2 to 6 are obtained as stated above. Herein, the muscle action data matrix R was 20×8.

The calculated principal component vector can be considered to correspond to the combination of the antagonistic muscle pair groups.

Figure 6A:
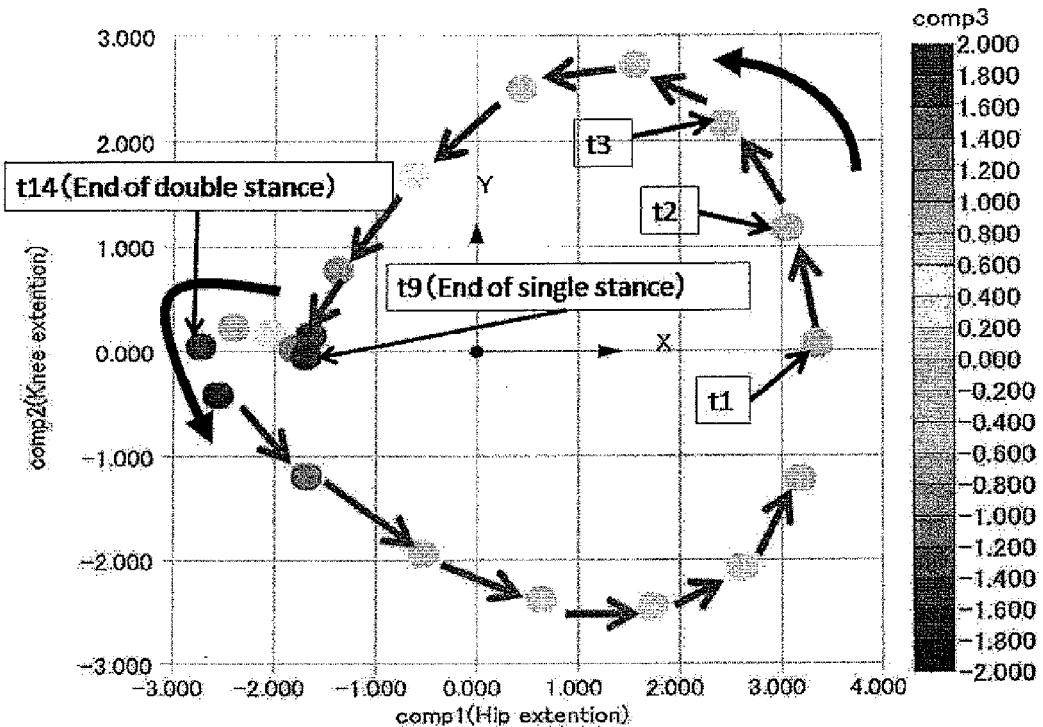
FIGS. 6A and 6B are diagrams illustrating principal component scores of three principal components having cumulative contribution of 90% or more for a matrix R where x axis, y axis and z axis represent a first principal component, a second principal component and a third principal component, respectively.
Figure 6B:
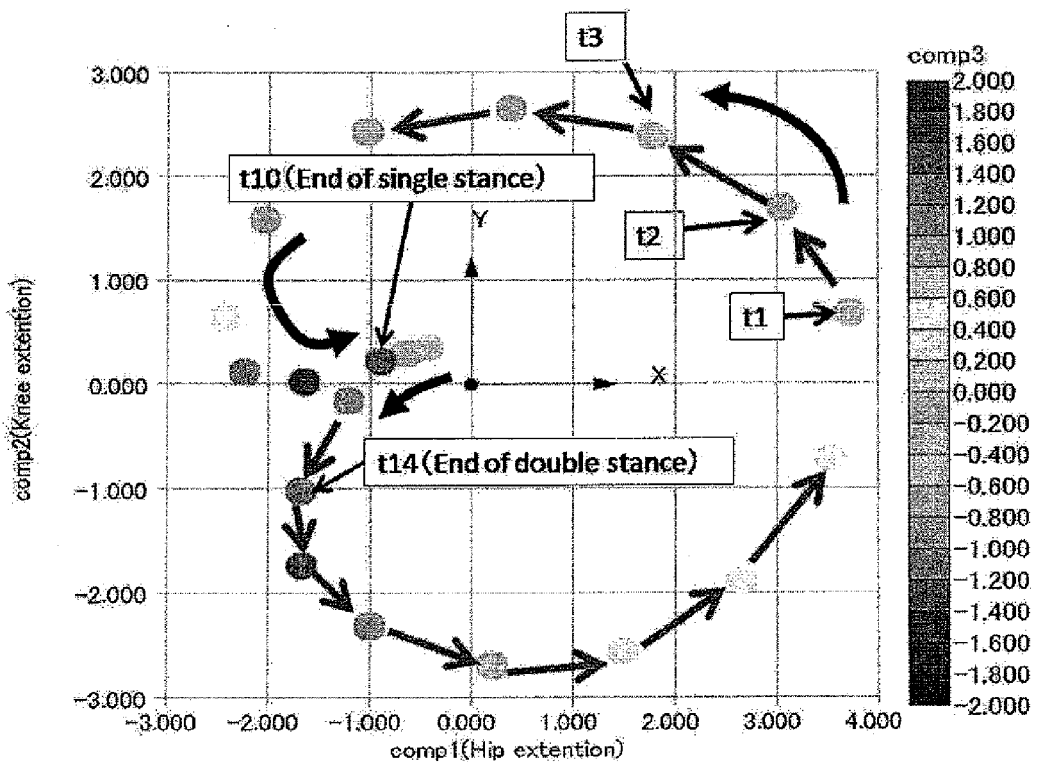
Figure 7A:
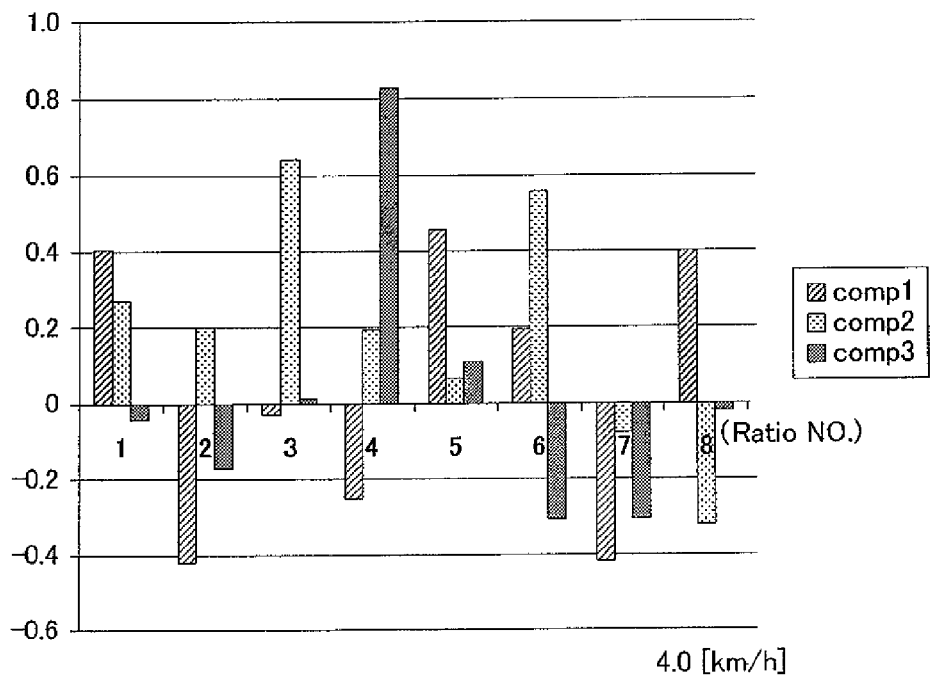
FIGS. 7A and 7B are diagrams representing elements of the principal components in FIGS. 6A and 6B in the order of the antagonistic muscle ratio No.
Figure 7B:
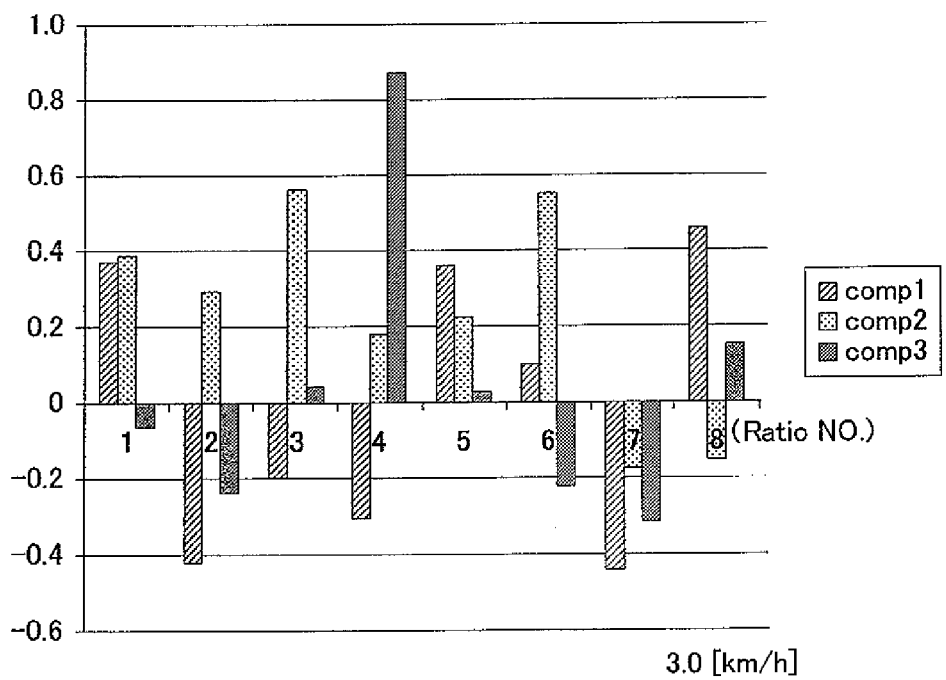

FIGS. 6A and 6B are diagrams illustrating principal component scores of three principal components having cumulative contribution of 90% or more for a matrix R where x axis, y axis and z axis represent a first principal component, a second principal component and a third principal component, respectively. FIGS. 7A and 7B are diagrams representing elements of the principal components in the order of the antagonistic muscle ratio No.

Other items are as follows.

[At the walking speed of 4.0 km/h]
Er={2.16, 1.80, 3.32, 1.56, 0.89, 2.85, 1.37, 0.96}
λ={4.62, 2.43, 0.91}
c={0.56, 0.29, 0.11}
C={0.56, 0.85, 0.96}
[At the walking speed of 3.0 km/h]
Er={2.10, 1.45, 3.20, 2.03, 0.99, 2.45, 0.98, 0.87}
λ={4.03, 2.76, 0.74}
c={0.49, 0.33, 0.09}
C={0.49, 0.82, 0.91}

In FIGS. 6A and 6B, the third principal component includes values ranging from −2.000 to 2.000 that are divided into twenty segments at every 0.200 in different colors for identification. In FIGS. 6A and 6B, each plot has time-series information as t1, t2, ... t20 attached thereto. Assigning the identification numbers from 1 (values −2.000 to −1.800) to 20 (values 1.800 to 2.000) from the lowest rank to the highest rank to different colored identification display, the identification numbers from t1 to t20 in FIG. 6A will be {10, 9, 8, 8, 9, 12, 15, 19, 19, 16, 11, 7, 3, 3, 5, 7, 9, 12, 12, 9}, and the identification numbers from t1 to t20 in FIG. 6B will be {11, 6, 7, 7, 7, 9, 13, 18, 19, 18, 13, 9, 8, 7, 6, 7, 9, 11, 13, 13}. Note here that, since the monitor 24 used actually is a color monitor, they can be simply identified with colors.

Figure 8A:
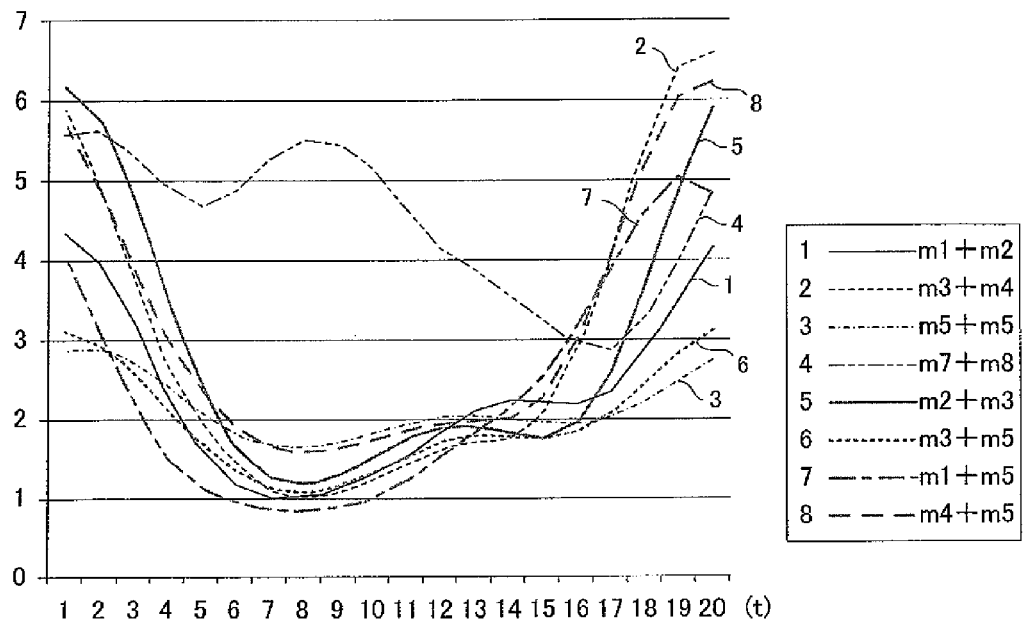
FIGS. 8A and 8B are diagrams indicating muscle activity.
Figure 8B:
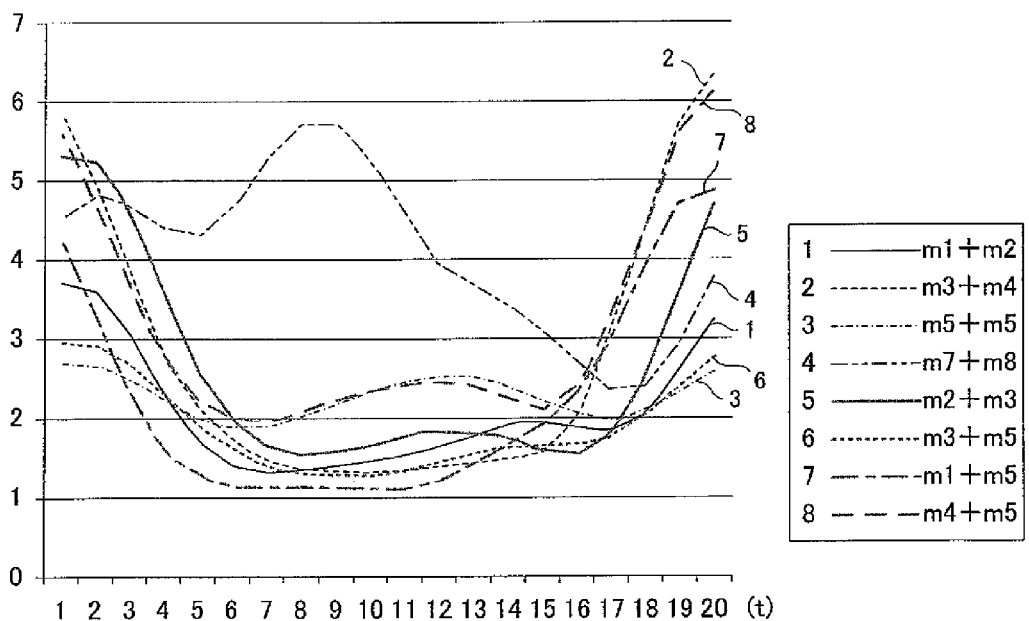
Figure 9A:
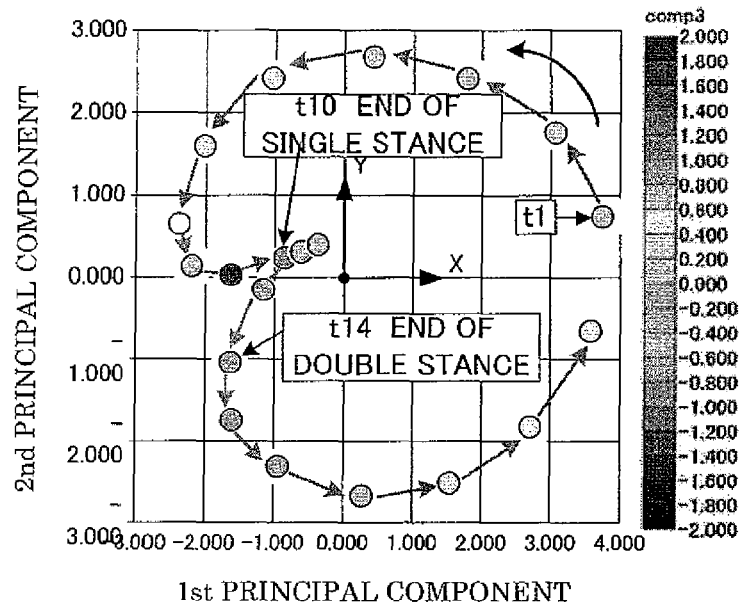
FIGS. 9A and 9B illustrate principal component scores of the antagonistic muscle ratios, and FIG. 9C illustrate a difference of first and second principal components, in this case, among the principal component scores of the antagonistic muscle ratios in FIGS. 9A and 9B.
Figure 9B:
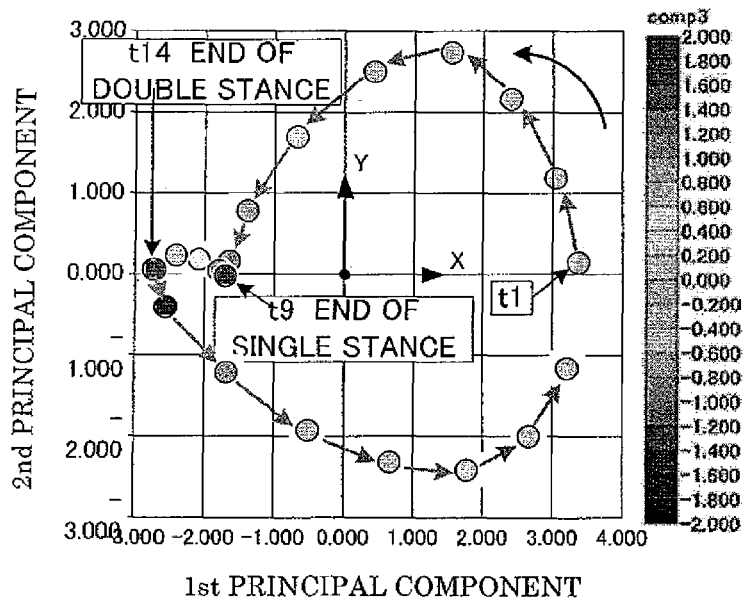
Figure 9C:
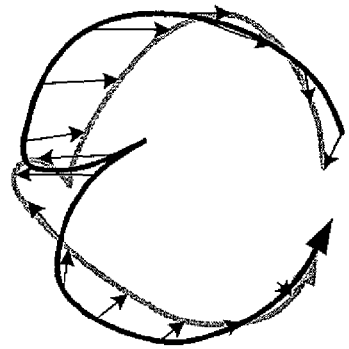

FIGS. 8A and 8B are diagrams indicating muscle activity. FIGS. 9A and 9B illustrate principal component scores of the antagonistic muscle ratios, and FIG. 9C illustrate a difference of first and second principal components, in this case, among the principal component scores of the antagonistic muscle ratios in FIGS. 9A and 9B. In FIGS. 6 to 8, FIGS. 6A, 7A, and 8A is for 4.0 km/h and FIGS. 6B, 7B, and 8B is for 3.0 km/h.

The display control unit 205 is configured to calculate a difference of the first principal component as time information and display the calculated difference with an arrow. In another possible drawing, between a plot position and another plot position having the same time of each piece of time information may be displayed a line segment, and an arrow may be provided from a reference side to a new measurement side.

(Consideration)

According to the report by G. Cappellini et al. ("Motor Patterns in Human Walking and Running", J Neurophysiol Vol. 95, p. 3426-3437, 2006.), myoelectric potential data on thirty-two muscles can be explained sufficiently with five timing patterns. In this processing, however, it was found that three principal components for eight types of antagonistic muscle ratios for eight muscles had cumulative contribution exceeding 90%, and standardized myoelectric potential data could be explained with three elemental basic patterns.

The following examines muscle coordination. Comparing the elements of the principal components having cumulative contribution exceeding 90% of the results of the principal component analysis for the matrix R with major functions of the antagonistic muscle ratios, it can be considered that the first principal component has a role of hip joint extension, the second principal component has a role of knee joint extension, and the third principal component has a role of ankle joint extension. A graph with X axis and Y axis representing the first principal component and the second principal component draws a characteristic shape closer to an ellipse. Bringing into correspondence with the gait phase, it can be found that the principal component scores vary at substantially constant intervals except for the double stance phase. It can be found that the third principal component increases in the vicinity of the double stance phase. From these results, it can be found that walking action can be explained by changing the weight of the three principal components. Positive and negative of these values also have an important meaning, and inversion of the signs means inversion of the action conceivably. That is, as for y axis, for example, when the phase is shifted from a stance phase to a swing phase, the sign of y axis is inversed. Bringing this into correspondence with the gait phase, it can be found that the action is inversed.

As for the muscle activity, the degree of action becomes higher for almost all antagonistic muscle pairs around heel strike. This is because joint stiffness is increased against possible disturbance at the moment of heel strike, and is associated with a characteristic of muscle action against impact from heel strike, which is typically said in the field of rehabilitation (Yoshihiro EHARA "Ningen no hokou, robotto no hokou" Keisoku to Seigyo (or "Human walking and robot walking", measurement and control) (in Japanese), Vol 45, p 1018-1023, 2006). Another report shows that when playing catch, muscle activity increases at antagonistic muscles of the wrist and elbow only before and after the moment when the hand comes into contact with a ball so as to get ready for impact by increasing joint stiffness (Theodore E. Milner: "Adaptation to destabilizing dynamics by means of muscle cocontraction", Exp Brain Res Vol 43, p. 406-416, 2002.), and similarity can be expected therefrom as well. In another characteristic respect, the activity of ankle joint antagonistic muscles only increases during single stance phase.

In the present experiment, myoelectric potentials of eight muscles at a right leg of a healthy male subject during walking were measured, and principal component analysis was conducted on the basis of antagonistic muscle ratios to find muscle coordination. As compared with the aforementioned report by G. Cappellini emphasizing timing of muscle action, the analysis result this time based on the antagonistic muscle ratio emphasizes muscle coordination during a motion. Conceivably the principal component analysis using these antagonistic muscle ratios is applicable to gait evaluation. Further the activity shows the possibility that safety is increased for disturbance.

In this way, it can be considered that functions of antagonistic muscles are very important for a joint motion.

Experiment 2

Experiment Method

Figure 10:
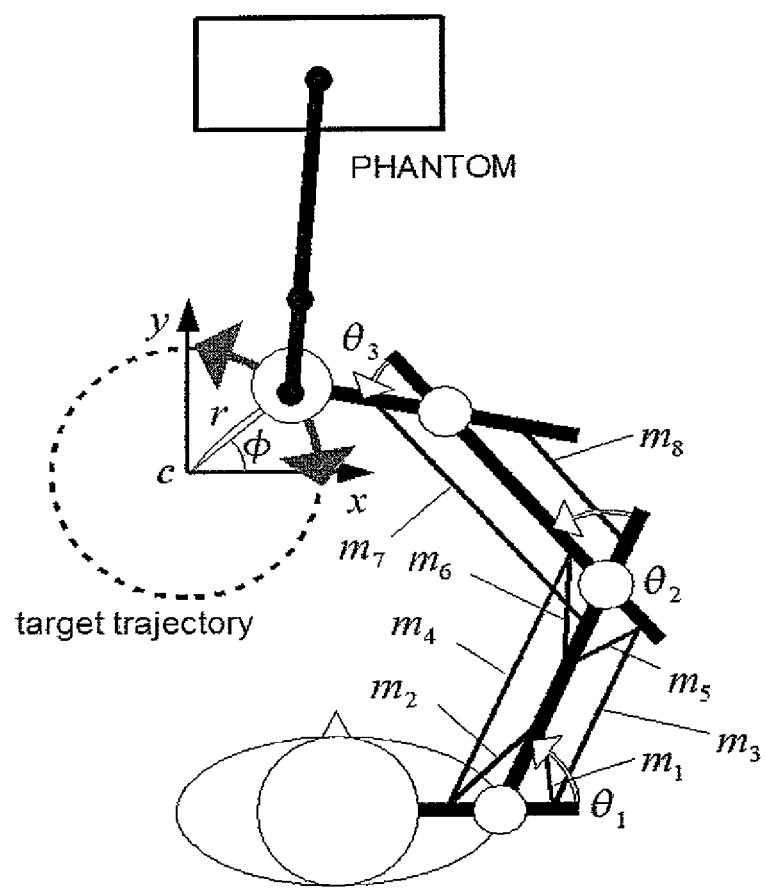
FIG. 10 is a diagram illustrating measurement results of EMG, hand positions and joint angles.

In the present experiment, a healthy male person (22 years old, right-handed) volunteered for a unique task of moving a hand clockwise along a circular trajectory in a plane without a constraint of the hand, and myoelectric potentials, hand positions and joint angles of him were measured (FIG. 10).

Table 2 shows the names of muscles undergone the myoelectric potential measurement.

TABLE 2

| Muscle number | |
|---|---|
| Muscle No. | Muscle name |
| $m_1$ | deltoid posterior |
| $m_2$ | deltoid anterior |
| $m_3$ | triceps long head |
| $m_4$ | biceps |
| $m_5$ | triceps latral head |
| $m_6$ | brachioradialis |
| $m_7$ | flexor carpi radialis |
| $m_8$ | extensor carpi ulnaris |

Table 3 illustrates definitions of parameters and attached points of the muscles.

TABLE 3

| Antagonistic muscle ratio and their function | | |
|---|---|---|
| Ratio No. | Pair | Function |
| $r_1$ | $m_1/m_2$ | Shoulder extention |
| $r_2$ | $m_4/m_3$ | (Shoulder flexion) & Elbow flexion |
| $r_3$ | $m_5/m_6$ | Elbow extention |
| $r_4$ | $m_8/m_7$ | (Elbow extention) & Wrist extention |

(Experimental Task)

Initial values of the hand position and the joint angles are as follows:

$(\phi, \theta_1, \theta_2, \theta_3) = (-\pi/2, \pi/2, \pi/2, 0)$.

(Experimental Task)

Although the hand was not constrained at all, the upper arm was held by hanging it from a sufficiently high ceiling to compensate for gravity. A target circular trajectory had a radius of 100 mm, and the examinee was instructed to move along the target circular trajectory as close as possible. Average values of x and y coordinates of all data are regarded as the rotation center, and a rotation center c and a phase angle θ are calculated after measurement. The position $\phi=0$ is regarded as a start position/end position of one trial. Then, the examinee was instructed to perform one trial in 8 to 10 seconds, and measurement data for six trials was obtained in 60 seconds.

(Myoelectric Potential Measurement)

Myoelectric potentials were measured using surface electrodes of 10 mm in size with the interelectrode distance set at 20 mm and the myoelectric potentials were amplified with a myoelectric potential acquisition device and a bio-amplifier WEB-9000 (produced by Nihon Kohden), and then were recorded via PowerLab8/30 (produced by ADInstruments) at a sampling frequency of 1 khz. Before attaching the electrodes to the examinee, the skin was treated with SkinPure (produced by Nihon Kohden) to lower skin resistance to 10 kΩ or less.

(Other Measurement Instrument)

The present experimental device (system) used PHANTOM as a force display device developed by SenSable Technologies (SensAble technologies:http://www.sensable.com/.). Note here that in the present motion (task), force display was not performed but hand position measurement only was performed. Joint angles were measured using Goniometer (produced by Biometrics), and the obtained voltage values were converted into angular values via an AD board (produced by Contec).

(Analysis)

In order to clarify a coordination relationship existing between muscles, antagonistic muscle ratios r1 to r4 defined in Table 4 were found, and the data underwent normalization for the length of one trial, and then principal component analysis was performed. The analysis procedure is described as follows.

TABLE 4

| | Result of PCA | | | |
|---|---|---|---|---|
| principal component | 1st | 2nd | 3rd | 4th |
| $r_1$ | −0.58 | −0.19 | 0.19 | −0.77 |
| $r_2$ | 0.08 | 0.95 | 0.14 | −0.26 |
| $r_3$ | 0.56 | −0.21 | 0.78 | −0.18 |
| $r_4$ | −0.58 | 0.12 | 0.58 | 0.56 |
| eigenvalue | 2.74 | 1.08 | 0.14 | 0.045 |
| proportion of variance | 0.68 | 0.27 | 0.03 | 0.01 |
| cumulative proportion | 0.68 | 0.95 | 0.99 | 1 |

(Calculation of % MVC and Antagonistic Muscle Ratios)

The obtained data on myoelectric potentials underwent rectification, filtering (50 to 150 Hz band-pass) and smoothing in this order, and then was normalized with values during the maximum isometric contraction measured beforehand and was converted into percentage to be % MVC. Further, in accordance with Table 4, antagonistic muscle ratios were found based on the values of % MVC.

(Normalization of Trials)

Since the time for one trial was not constant, normalization was performed for each trial time. Further, each trial was divided temporally into twenty-five sections, which were defined as t1, t2, ... t25. Then, data for the time sections were averaged to find an average value of all trials, and the thus obtained data was dealt with as a representative data.

(Principal Component Analysis on Antagonistic Muscle Ratio)

Among representative data, four columns representing antagonistic muscle ratios were extracted. The extracted data with 25 rows and 4 columns underwent principal component analysis, and the resultant was used for human motion analysis based on antagonistic muscle ratios.

(Results)

Figure 11:
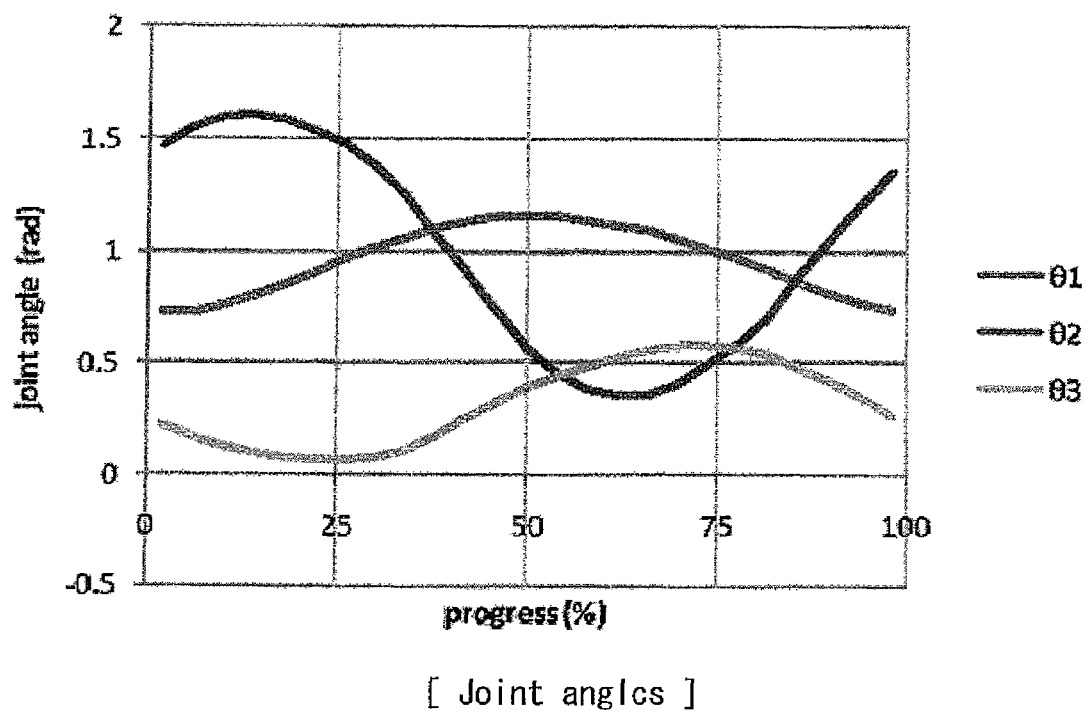
FIG. 11 is a diagram illustrating progress of each joint angle.
Figure 12:
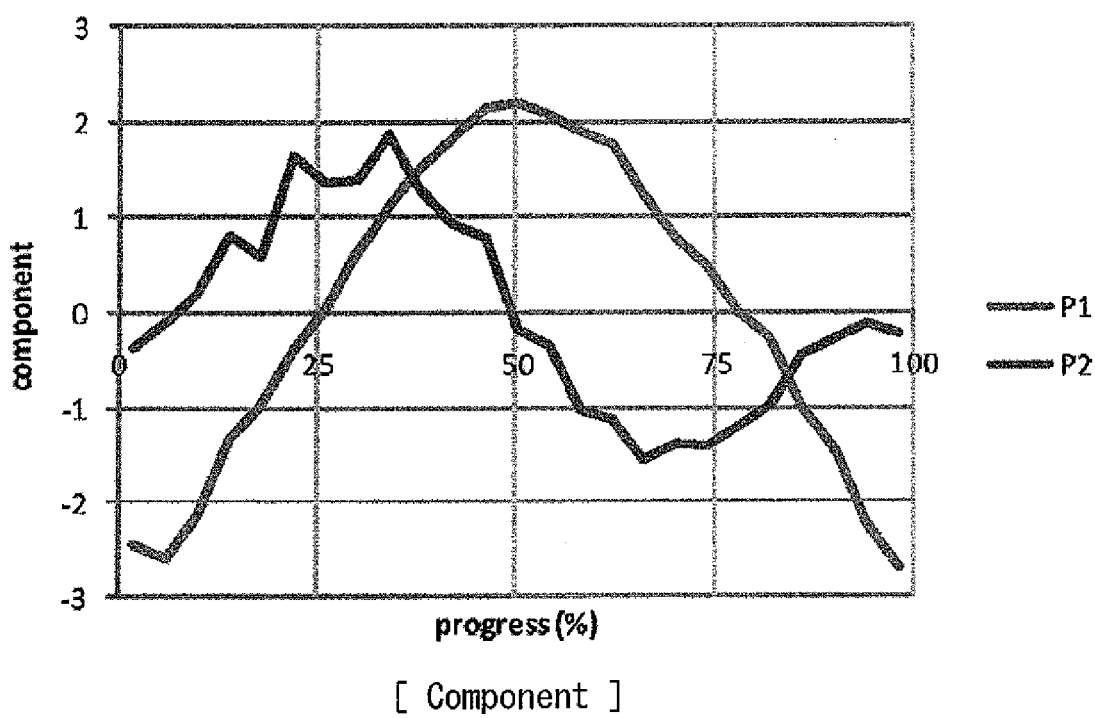
FIG. 12 is a diagram illustrating progress of principal component scores.
Figure 13:
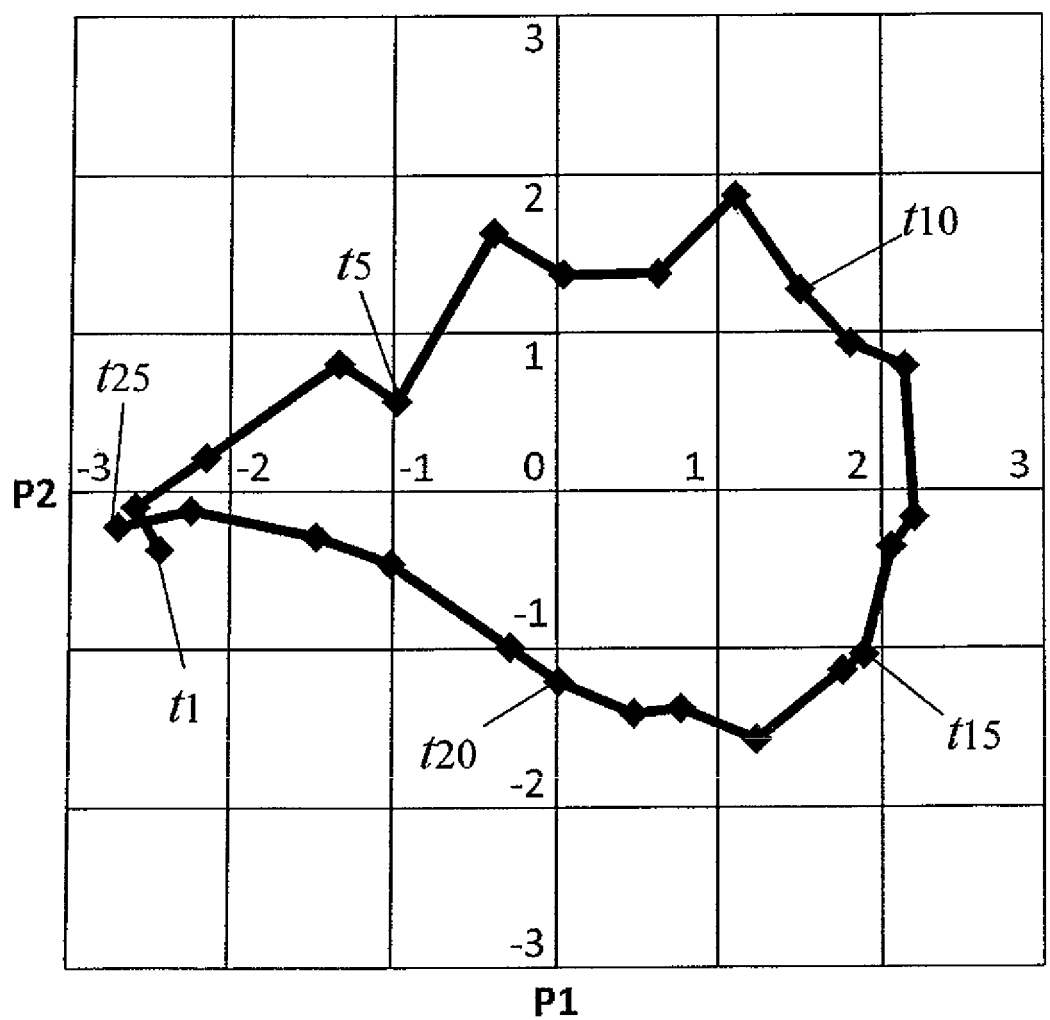
FIG. 13 is a diagram illustrating the state where the first principal component scores are plotted on the horizontal axis and the second principal component scores are plotted on the vertical axis.

Table 4 shows the results of the principal component analysis. Herein, P1 denotes the first principal component score, and similarly P2, P3 and P4 denote the second and later components. FIG. 11 illustrates progress of each joint angle, FIG. 12 illustrates progress of principal component scores and FIG. 13 illustrates the state where the first principal component scores are plotted on the horizontal axis and the second principal component scores are plotted on the vertical axis. In FIG. 13, time sections are labeled every 5 points.

(Consideration)

The result obtained shows that cumulative contribution up to the second principal component reached 95% or more. Therefore, the following consideration focuses on the principal component scores of the first principal component and the second principal component and principal component vectors thereof.

Since the motion (task) performed in the present experiment is a slow movement in a plane, it can be considered that the respective joint angle parameters, i.e., an antagonism of muscal to maintain the hand position was generated. Comparing between θ1 and P1 and between θ2 and P2, the graph of the principal component scores and the graph of angles matched substantially in phase, and such a consideration can be verified based on this result as well.

Next, the first principal component and the second principal component are considered as follows. Firstly, as for the first principal component, since the principal component scores get closer to 0 in the vicinity of $\phi=\pi/2$ and $\phi=-\pi/2$, and get closer to the maximum value in the vicinity of $\phi=\pi$ and to the minimum value in the vicinity of $\phi=0$. Accordingly, it was found that the component governs the motion in the direction orthogonal to the horizontal direction or the direction connecting the motion base part and the motion end part (deflection angle direction). For instance, since $\phi=0$ is the rightmost position on the circular trajectory where the shoulder joint extends most, the result can be considered reasonable.

Next, considering the second principal component similarly to the first principal component, this component governs the motion in the back-and-force direction or the direction connecting the motion base part and the motion end part (radius direction). For instance, since $\phi=\pi/2$ is the nearest position on the circular trajectory, this result can be considered reasonable.

Except for the vicinity of $\phi=0$, the principal component scores P1 and P2 are platted in a substantially perfect circle form. It is interesting to consider this in association with the hand position.

In the present experiment, the task moving along a circular trajectory clockwise in a plane was focused on, and motion analysis was performed thereto using antagonistic muscle ratios as one example. Then, on the basis of the antagonistic muscle ratios, muscle coordination was described. In the apparatus (system) used in the present experiment, PHANTOM was used, thus enabling the experiment with high degree of flexibility. PHANTOMPremium3.0/6DOF can exert the maximum force at 22 [N] in a working space, and can generate a three-dimensional force field. The system can measure not only a task in a plane but also a three-dimensional motion, and therefore conceivably a wide range of motion analysis about upper limbs can be expected using the present apparatus (system).

The present invention can use the following embodiments.

(1) In the present embodiment, required motions (tasks) of arms and legs are targeted. The present invention, however, is not limited to them, and is applicable to predetermination motions (tasks) at joint parts with antagonistic muscle pairs.

(2) In the present embodiment, a camera was used for gait phase judgment. The camera, however, is not must, and a gait phase may be set using time information and the like.

(3) In the present embodiment, the reference and differential signals obtained from the subject may be supplied to the actuator 31 of the robot 30 of FIG. 1, whereby coaching of a predetermined motion (task) can be preferably performed in an actual motion using the robot 30 as compared with the case of observing the difference state with the monitor 24.

(4) In the present embodiment, a difference in each principal component score was displayed on the monitor 24. However, an electric stimulus signal at a level corresponding to this difference may be given to a required part (muscle) of the subject, whereby the present invention is applicable to a functional electric stimulus system configured to bring a predetermined motion (task) of the subject to ideal one (reference one).

Figure 14:
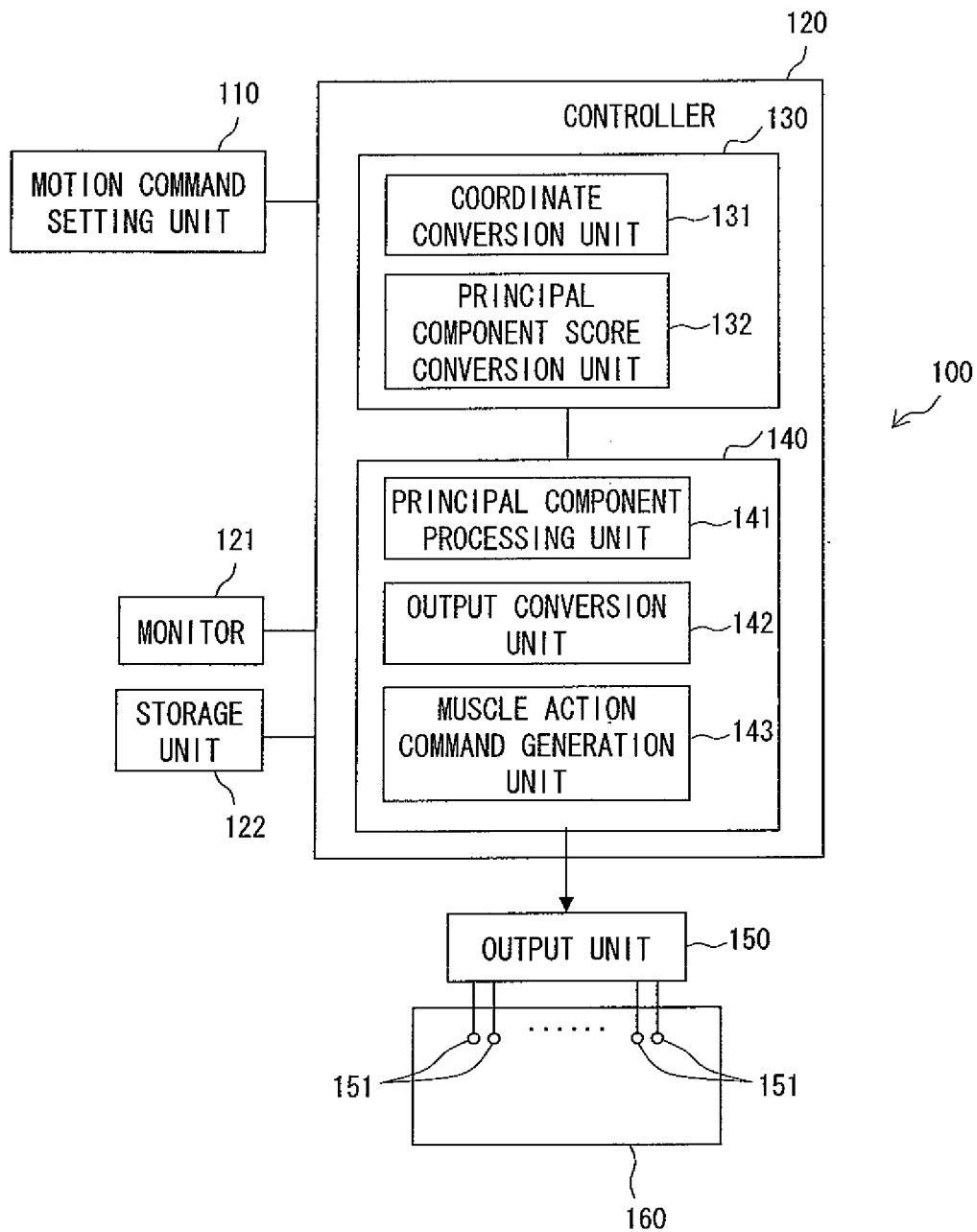
FIG. 14 illustrates an exemplary configuration of a muscle synergy interface according to the present invention.
Figure 15:
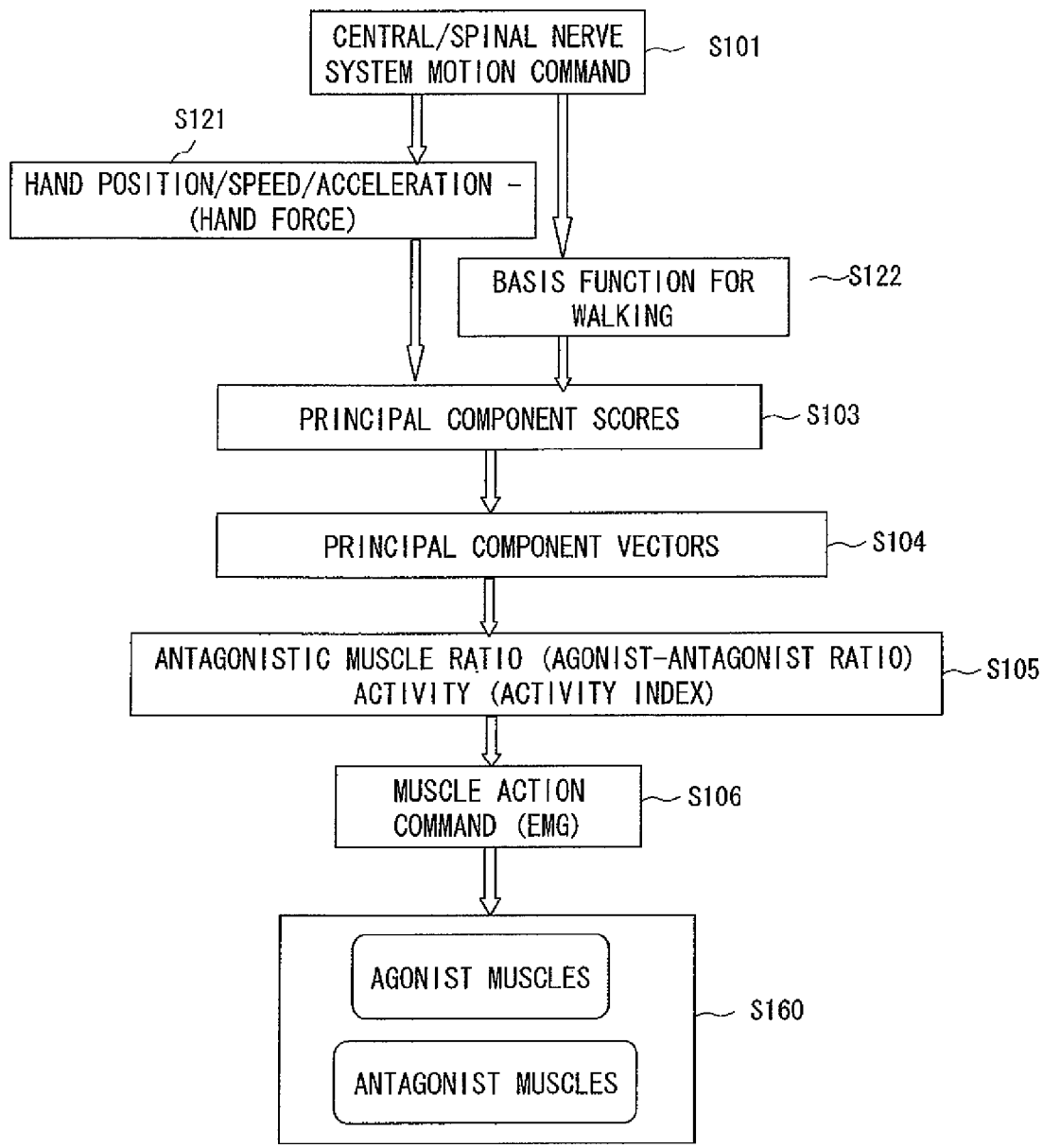
FIG. 15 is a flowchart illustrating the outline of the procedure executed by the muscle synergy interface according to the present invention.

FIG. 14 illustrates an exemplary configuration of a muscle synergy interface according to the present invention. FIG. 15 is a flowchart illustrating the outline of the procedure executed by the muscle synergy interface according to the present invention.

A muscle synergy interface 100 includes: a motion command setting unit 110 that instructs a control target 160 about a motion; and a controller 120 including a microcomputer or the like. The controller 120 includes: a first conversion unit 130 that converts a command from the motion command setting unit 110 into principal component information; and a second conversion unit 140 that converts the principal component information obtained by the first conversion unit 130 into a signal to make the control target 160 perform a motion. The muscle synergy interface 100 further includes an output unit 150 that outputs a signal obtained by the second conversion unit 140 as a potential signal for a motion instruction.

The control target 160 may be a person to undergo rehabilitation (human). In the case of a human, electrodes 151, 151 are attached on a skin surface facing a target muscle, and a potential signal from the output unit 150 is to output to these electrodes 150. In the present embodiment, the potential signal is generated for each antagonistic muscle pair as stated later. The control target 160 assumed may be a gear (such as a power suit) to assist a human motion (for rehabilitation), a robot or the like. In the case of a gear or a robot, it has a plurality of actuators such as artificial muscles to move a required part of a mechanical body. Actuators may be configured with a McKibben-type artificial muscle, for example, configured to control a pneumatic pressure in accordance with an electric signal to allow a pneumatic rubber tube to expand or contract, and the actuators receive a signal from the output unit 150 as a potential signal (driving signal) for operation. The actuators are not limited to a McKibben-type artificial muscle, and may be an electro-mechanical converter such as an electromagnetic solenoid, a piezo-electric device or a motor that generates a mechanical motion from an electrical signal or using another force obtained by converting an electrical signal.

The motion command setting unit 110 is provided with at least a configuration allowing information as a motion command to be input, e.g., an input unit including a keyboard, a mouse or the like. The motion command setting unit 110 is configured to output motion information specifying an input motion as position information typically. The position information specifies a motion mode on an axis or in a plane with rectangular coordinates as described later.

The controller 120 further may include a monitor 121 so as to enable checking of input data or data being processed. The controller 120 further includes a required storage unit 122 including a ROM storing a control program and basic data and a RAM temporarily storing information being processed.

The first conversion unit 130 includes a coordinate conversion unit 131 that converts position information on rectangular coordinates set by the motion command setting unit 110 into polar coordinates, and a principal component score conversion unit 132 that specifies a relationship between the polar coordinates and principal component information. The second conversion unit 140 includes a principal component processing unit 141 that converts principal component score information into a principal component, an output conversion unit 142 that converts a principal component into an antagonistic muscle ratio and activity, and a muscle action command generation unit 143 that creates, based on the antagonistic muscle ratio and activity, a potential signal at a level to be applied to an agonist muscle and an antagonist muscle making up an antagonistic muscle pair.

In FIG. 15, at Step S101, the motion command setting unit 110 sets hand position information (x, y), for example, as target motion information. Information set at Step S101 may contain, in addition to the position information, a motion speed, acceleration as well as dynamic interference in the case of a high motion speed and accessory information when predetermined constraint is present to control a hand motion (hand force), for example. The target motion information input by the motion command setting unit 110 may contain, in addition to information to specify a hand motion, information to specify a walking motion as well as position information and preferable information to specify a motion depending on the motion. For instance, for information on a walking motion, walking speed information and stride information may be used. Such information may be information to specify a toe position.

At Step S121, motion information for hand as stated above is set, and at Step S122, motion information for walking as stated above is set. A basis function for walking refers to a basic function to describe a walking motion. At Step S103, a principal component score is obtained. At Step S104, a principal component is created from the obtained principal component score. At Step S105, the principal component is converted into an agonistic muscle ratio and activity. At Step S160, a potential signal to be applied to an agonist muscle and an antagonist muscle for each antagonistic muscle pair is generated and is output to a corresponding electrode 151.

The procedure illustrated in FIG. 15 is roughly divided into the processing from Step S101 to Step S103 and from Step S104 to Step S106. The processing from Step S101 to Step S103 is referred to as first conversion processing and the processing from Step S104 to Step S106 is referred to as second conversion processing.

Firstly, the second conversion processing from Step S104 to Step S106 is described below. This second conversion processing has been already proposed by the present inventors in Japanese Patent Application Laid-Open No. 2009-212149.

That is, the second conversion processing is to generate a potential signal as a muscle action command to each of an agonist muscle and an antagonist muscle making up each antagonistic muscle pair from principal component information obtained by multivariate analysis and output the potential signal. This processing is based on high correlation existing between a potential signal level applied to each muscle of an antagonistic muscle pair and principal component information.

Figure 17:
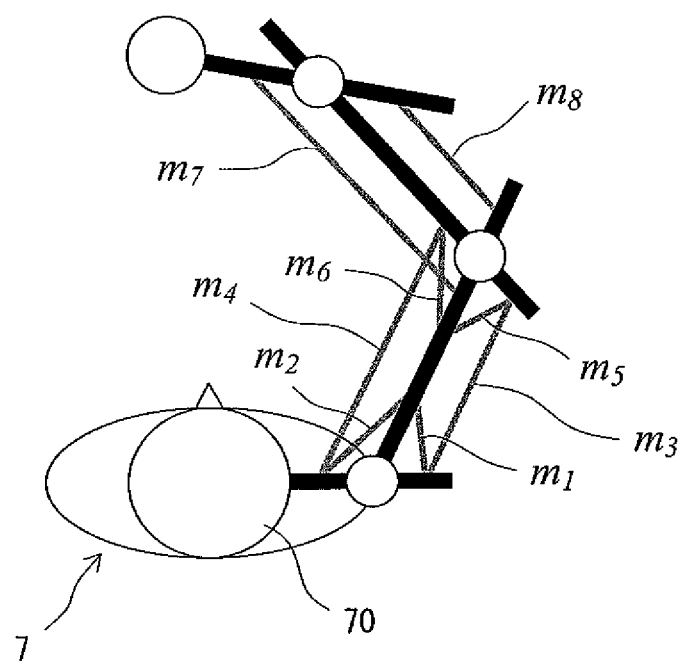
FIG. 17 is a schematic view of muscles illustrating a positional relationship among muscles from a head or a shoulder to a hand of an examinee and a relationship of antagonistic muscle pairs.

In Japanese Patent Application Laid-Open No. 2009-212149, a subject was instructed to perform a predetermination motion operation such as a circular motion of an upper limb in a horizontal plane or a walking motion by a lower limb, and during such a motion, a potential of a muscle acting was detected via an electrode attached to the skin facing the muscle. Multivariate analysis was then conducted to the detected potential of each muscle to extract a principal component. For instance, as illustrated in FIG. 17, myoelectric potentials of anterior deltoid fiber (m1) . . . extensor carpi ulnaris (m8) from shoulder to hand were converted into an antagonistic muscle ratio and an activity of each antagonistic muscle pair representing a coordination relationship of the muscles, and on the basis of these antagonistic muscle ratio and activity of each antagonistic muscle pair, multivariate analysis was executed to calculate first, second, third . . . principal components so as to extract principal components having contribution exceeding a predetermined %, preferably about 90%. In this upper limb circular motion, the first and second principal components had cumulative contribution exceeding 90%. Therefore principal component scores for the first and second principal components were found, and further principal component vectors therefor were found, whereby a potential signal having high correlation was generated to an agonist muscle and an antagonist muscle of each antagonistic muscle pair as a force contributing to the motion.

Further, the subject was instructed to perform a walking motion using lower limbs, and during such a motion, a potential of a muscle acting was detected via an electrode attached to the skin facing the muscle. Multivariate analysis was then conducted to the detected potential of each muscle to extract a principal component. For instance, eight muscles from the root of legs and toes including a pair of a flexor and an extensor of hip joint mono-articular muscles, hip joint/knee joint bi-articular muscles, knee joint mono-articular muscles and ankle joint muscles were targeted. The detected myoelectric potentials were converted into an antagonistic muscle ratio and an activity of each antagonistic muscle pair, and on the basis of these antagonistic muscle ratio and activity of each antagonistic muscle pair, multivariate analysis was executed to calculate first, second, third . . . principal components so as to extract principal components having contribution exceeding a predetermined %, preferably about 90%. In this lower limb walking motion, the first and second principal components have cumulative contribution exceeding 80% at least. Therefore principal component scores for the first and second principal components were found, and further principal component vectors therefor were found, whereby a potential signal having high correlation was generated to an agonist muscle and an antagonist muscle of each antagonistic muscle pair as a force contributing to the motion.

In this way, when muscles governing a motion and the contents of the motion (in the above examples, the upper limb circular motion and the lower limbs walking motion) are decided beforehand, then principal component information to specify the motion can be decided. Then, using principal component information decided beforehand, the first conversion processing (Step S101 to S103 in FIG. 15) including the processing to obtain a principal component score from the contents of the motion can be performed. The following describes this processing.

Once the motion contents are decided, a type of a principal component corresponding thereto can be decided. For instance, in the case of an upper limb motion in a horizontal plane, first and second principal components are decided beforehand with predetermined cumulative contribution. Then as described later, if there is any correlation between a motion command and a principal component, such correlation can be used to conduct a series of processing using principal component information to generate a potential signal easily and promptly from Step S101 to Step S016 in FIG. 15 without executing complex calculation of analyzing the motion command and generating a potential signal to each muscle.

Then, a relationship between the contents of a motion command and a principal component corresponding to the motion is described below. A motion command is generated at a cerebrum motor area and is defined as a target position (x, y) describing motion contents. In the case of such an upper limb motion in a horizontal plane, the motion is defined as a target hand position (x, y).

Herein, analyzing this horizontal in-plane motion using an upper limb, such a motion can be described with contraction (distance r) along a line connecting the shoulder and the hand and rotation (angle θ) of the hand about the shoulder or the head. As a result of a principal component analysis about detected myoelectric potentials in a reaching motion task and a crank rotation task, it can be found that motion commands have such two types of meaning in many cases.

That is, the hand motion command can be represented with a polar coordinate (r, θ). Since the hand motion as a target is represented by rectangular coordinates at a cerebrum motor area, conceivably coordinate conversion is performed to polar coordinates at the central/spinal nerve system. Considering, as the hand motion information, a speed, acceleration as well as dynamic information and accessary information such as a force of a hand influencing on the environment and moment in addition to the target hand position, the flow of motion command generation in the horizontal in-plane motion using an upper limb will be as in FIG. 16.

Figure 16:
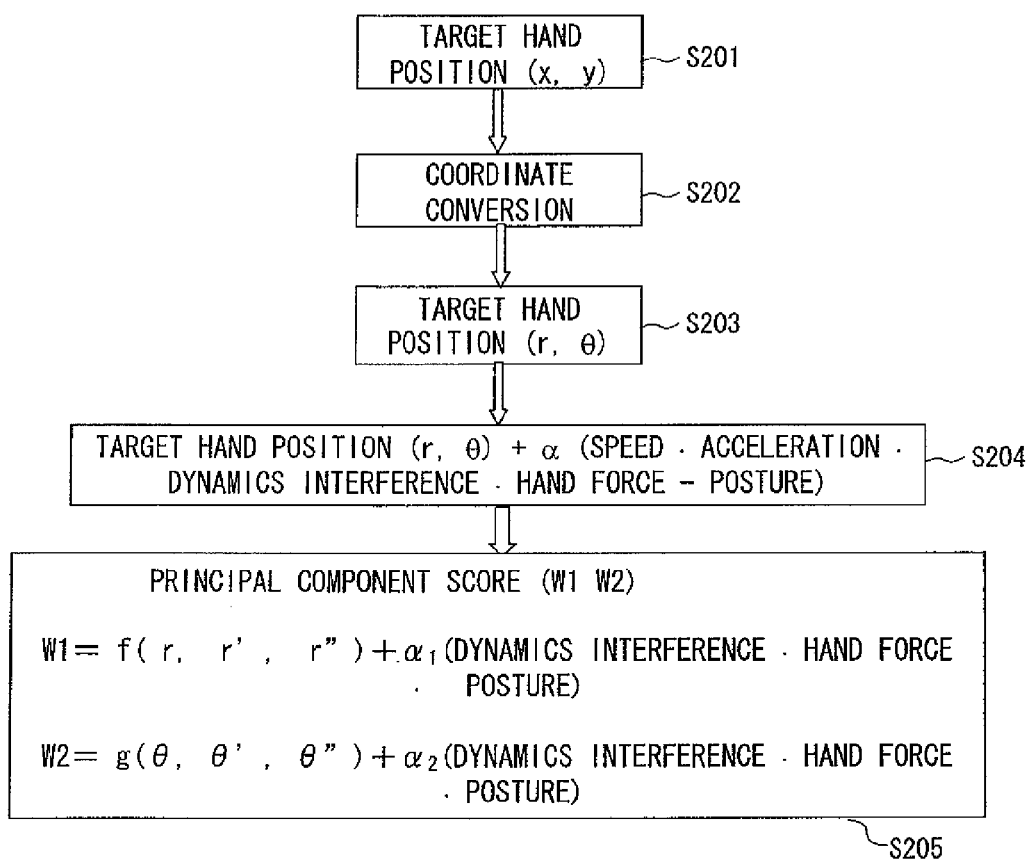
FIG. 16 is a flowchart describing the flow of motion command generation in the horizontal in-plane motion using an upper limb.

FIG. 16 is a flowchart describing the flow of motion command generation in the horizontal in-plane motion using an upper limb. In FIG. 16, firstly at Step S201, the motion command setting unit 110 sets a target hand position (x, y). The target position may be set by directly inputting coordinates or by storing motion contents (coordinates information) in association with identification information beforehand and designating identification information so as to designate the corresponding motion contents. In the latter case, the motion contents may be stored in the storage unit 122 in the controller 120. Since the motion contents contain not only the position information but also a motion speed, the motion contents are preferably configured to allow necessary accessary information to be designated.

At Steps S202 and S203, the target hand position (x, y) is converted into polar coordinates (r, θ) by using a well-known rectangular coordinates-polar coordinates conversion equation. At Step S204, the target hand position (r, θ)+α (speed·acceleration·dynamic interference·hand force·posture) is obtained, including accessary matters.

Then, at Step S205, scores (w1, w2) for each principal component are calculated. More specifically, they can be represented as:

$$w1 = f(r, r', r'') + \alpha 1 \text{ (dynamic interference, hand force, posture)}$$

$$w2 = g(\theta, \theta', \theta'') + \alpha 2 \text{ (dynamic interference, hand force, posture)}.$$

Herein, the sign ' indicates primary differential calculus and " indicates second differential calculus. In these expressions, the second differential calculus terms do not always exist, and in other examples a third differential calculus term may be required. Herein, the principal component W1 corresponds to the distance r of the polar coordinates, and the principal component w2 corresponds to the angle θ of the polar coordinates. The same goes for lower limbs during walking, and the motion command thereof can be represented with the polar coordinates (r, θ), and the toes positions with reference to the waist represented with the polar coordinates (r, θ) correspond to (w1, w2).

Subsequently, experimental results are described below. Table 5 illustrates the name of eight muscles as a target of myoelectric potential measurement in the present experiment and their corresponding electrode attachment positions.

TABLE 5

| Muscle No. | Japanese name | English name |
|---|---|---|
| m1 | 三角筋前部繊維 | deltoid posterior |
| m2 | 三角筋後部繊維 | deltoid anterior |
| m3 | 三頭筋長頭 | triceps long head |
| m4 | 二頭筋 | biceps |
| m5 | 三頭筋側頭 | triceps latral head |
| m6 | 腕橈骨筋 | brachioradialis |
| m7 | 橈側手根屈筋 | flexor carpi radialis |
| m8 | 尺側手根伸筋 | extensor carpi ulnaris |

The following Table 6 shows definitions of the antagonistic muscle ratios.

TABLE 6

| Ratio No. | Pair | Function |
|---|---|---|
| r1 | m1/m2 | Shoulder extention |
| r2 | m4/m3 | Shoulder flexion & Elbow flexion |
| r3 | m5/m6 | Elbow extention |
| r4 | m8/m7 | Elbow extention & Wrist extention |

FIG. 17 is a schematic view of muscles illustrating a positional relationship among muscles from a head 70 or a shoulder to a hand of an examinee 7 and a relationship of antagonistic muscle pairs.

(Experimental Task)

The examinee performed a task moving a hand position along a target circular trajectory with a radius of 100 mm in a plane, and the hand position was measured using a camera or the like and myoelectric potentials were measured. In order to compensate for gravity, the upper arm was held by hanging it from a sufficiently high ceiling.

Experiment Result 1

Figure 18:
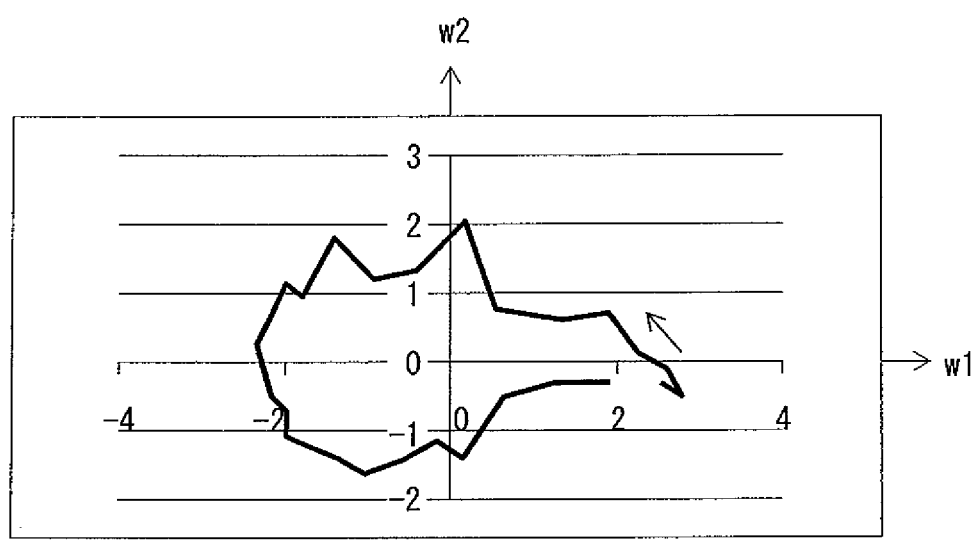
FIG. 18 is a diagram representing a motion position (time passage; see the arrow in the diagram) of the point (w1, w2) during the circular motion of a hand clockwise in a horizontal plane, where a cross axis represents the first principal component w1 and a vertical axis represents the second principal component w2.

The principal component vectors (two principal components having cumulative contribution of 90% or more) in the clockwise motion and the principal component scores have a relationship as in Table 7 and FIG. 18.

In this experiment, myoelectric potentials were measured, for example, using surface electrodes of 10 mm in size with the interelectrode distance set at 20 mm and were amplified with a myoelectric potential acquisition device and a bio-amplifier WEB-9000 (produced by Nihon Kohden), and then were recorded via PowerLab8/30 (produced by ADInstruments) at a sampling frequency of 1 khz. Before attaching the electrodes 151 to the examinee, the skin was treated with SkinPure (produced by Nihon Kohden) to lower skin resistance to 10 kΩ or less. The present experimental device (system) used PHANTOM that is a force display device developed by SenSable Technologies (SensAble technologies: http://www.sensable.com/). Note here that in the present motion (task), force display was not performed but hand position measurement only was performed. Joint angles were measured using Goniometer (produced by Biometrics), and the obtained voltage values were converted into angular values via an AD board (produced by Contec). In order to clarify a coordination relationship existing between muscles, antagonistic muscle ratios r1 to r4 defined in Table 6 were found, and the data underwent normalization for the length of one trial and then principal component analysis. The obtained data on myoelectric potentials underwent rectification, filtering (50 to 150 Hz band-pass) and smoothing in this order, and then was normalized with values during the maximum isometric contraction measured beforehand and was converted into percentage to be % MVC (% Maximum Voluntary Contraction). Further, in accordance with Table 6, antagonistic muscle ratios were found based on the values of % MVC.

TABLE 7

| first principal component | second principal component |
|---|---|
| 0.5807 | −0.1953 |
| −0.0919 | 0.9472 |
| −0.5635 | −0.2137 |
| 0.5804 | 0.1380 |

It was found from Table 7 that first and third elements (0.5807, −0.5635) of the first principal component vector represent shoulder extension (+) and elbow flexion (−) and the first principal component corresponds to expansion and contraction (r) along the line connecting the shoulder and the hand. Meanwhile, it was found that a second element (0.9472) of the second principal component vector represents simultaneous flexion (+) of the shoulder and the elbow with a bi-articular muscle, and so the second principal component corresponds to rotation (θ) of the hand around the shoulder or the head. FIG. 18 is a diagram representing a motion position (time passage; see the arrow in the diagram) of the point (w1, w2) during the circular motion of the hand clockwise in a horizontal plane, where a cross axis represents the first principal component w1 and a vertical axis represents the second principal component w2.

The principal component vectors in the counterclockwise motion were confirmed to become similar to the above. That is, the principal component vectors (two principal components having cumulative contribution of 90% or more) and the principal component scores have a relationship as in Table 8 and FIG. 19.

TABLE 8

| first principal component | second principal component |
|---|---|
| 0.6216 | −0.1137 |
| −0.1191 | 0.8141 |
| −0.4704 | −0.5499 |
| 0.6150 | −0.1479 |

Figure 19:
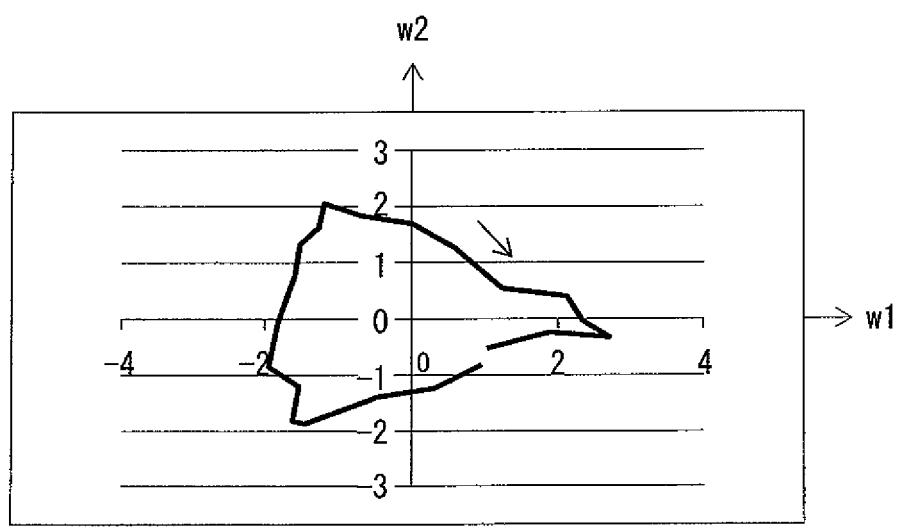
FIG. 19 is a diagram representing a motion position (time passage; see the arrow in the diagram) of the point (w1, w2) during the circular motion of a hand counterclockwise in a horizontal plane, where a cross axis represents the first principal component w1 and a vertical axis represents the second principal component w2.

It was found from Table 8 that first and third elements (0.6216, −0.4704) of the first principal component vector represent shoulder extension (+) and elbow flexion (−) and the first principal component corresponds to expansion and contraction (r) along the line connecting the shoulder and the hand. Meanwhile, it was found that a second element (0.8141) of the second principal component vector represents simultaneous flexion (+) of the shoulder and the elbow with a bi-articular muscle, and so the second principal component corresponds to rotation (θ) of the hand around the shoulder or the head. FIG. 19 is a diagram representing a motion position (time passage; see the arrow in the diagram) of the point (w1, w2) during the circular motion of the hand counterclockwise in a horizontal plane, where a cross axis represents the first principal component w1 and a vertical axis represents the second principal component w2.

Experimental Result 2

Figure 20:
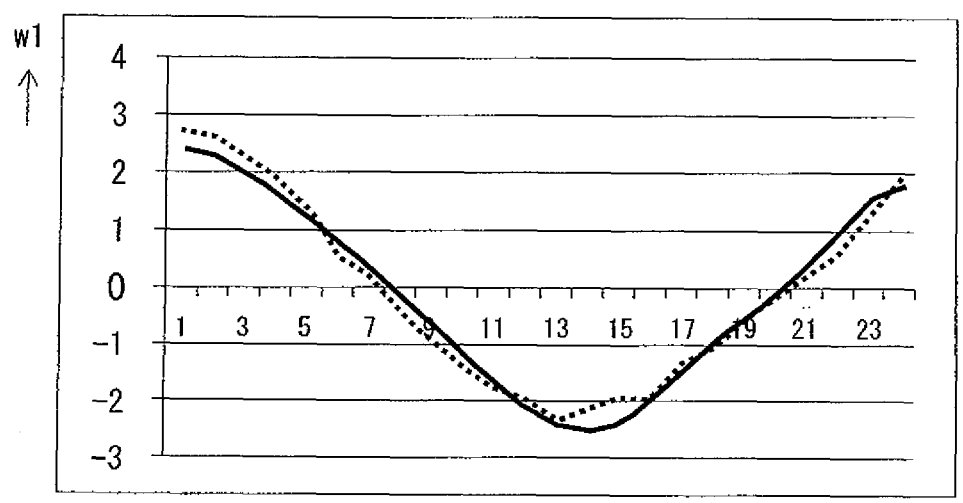
FIG. 20 is a diagram of a multiple regression analysis result indicating that the first principal component score w1 corresponds to the expansion and contraction (r) along the line connecting the shoulder and the hand.

FIG. 20 is a diagram of a result of a multiple regression analysis indicating that the first principal component score w1 corresponds to the expansion and contraction (r) along the line connecting the shoulder and the hand. The horizontal axis represents a motion position (time) and the vertical axis represents w1, where the dotted lines represent values based on the experiment and the solid line is obtained by the multiple regression analysis. An estimation result of w1 with (r, r') in the crank task (clockwise) is represented in Expression 7:

$$w1 = -0.02r - 0.05r' + 12.6 \qquad \text{(Expression 7)}$$

Figure 21:
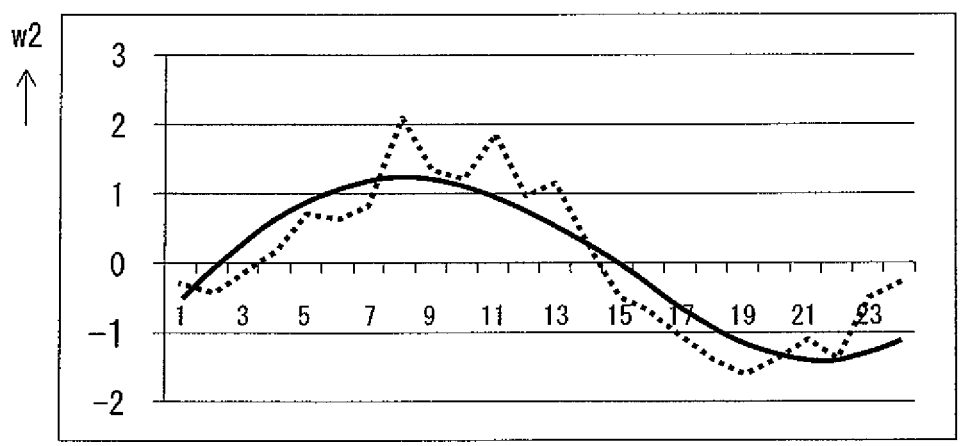
FIG. 21 is a diagram of a multiple regression analysis result indicating that the second principal component score w2 corresponds to the rotation (θ) of the hand around the shoulder or the head.

FIG. 21 is a diagram of a result of a multiple regression analysis indicating that the second principal component score w2 corresponds to the rotation (θ) of the hand around the shoulder or the head. The horizontal axis represents a motion position (time) and the vertical axis represents w2, where the dotted lines represent values based on the experiment and the solid line is obtained by the multiple regression analysis. An estimation result of w2 with (θ,θ') in the crank task (clockwise) is represented in Expression 8:

$$w2 = 6.5\theta + 7.7\theta' - 15.3 \qquad \text{(Expression 8)}$$

As illustrated in FIGS. 20 and 21, both of the curves w1 and w2 obtained by the multiple regression analysis are approximate to the principal component scores obtained by the multivariate analysis using the measurement values, and it was found that they have high correlation.

Experimental Result 3

Figure 22:
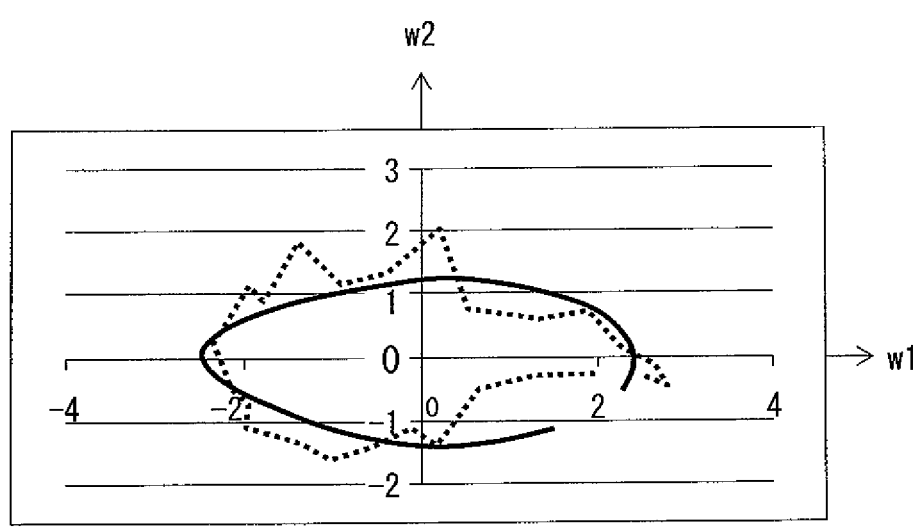
FIG. 22 is a diagram illustrating an estimation result (using the aforementioned multiple regression analysis) of clockwise (w1, w2) from the experimental value (r, θ) in the crank task (clockwise).
Figure 23:
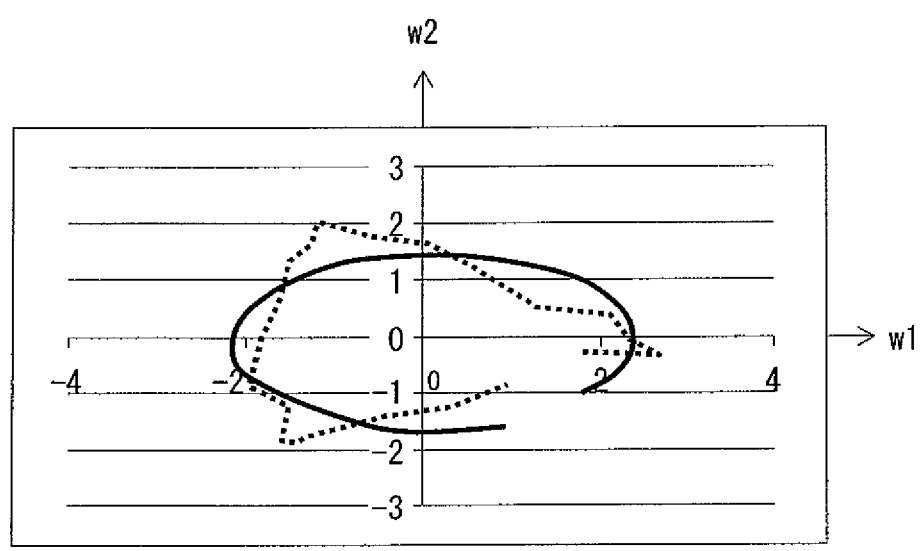
FIG. 23 is a diagram illustrating an estimation result (using the aforementioned multiple regression analysis) of counter-clockwise (w1, w2) from the experimental value (r, θ) in the crank task (clockwise).

FIG. 22 is a diagram illustrating an estimation result (using the aforementioned multiple regression analysis) of (w1, w2) in the clockwise from the experimental value (r, θ) in the crank task (clockwise). FIG. 23 is a diagram illustrating an estimation result (using the aforementioned multiple regression analysis) of (w1, w2) in the counterclockwise from the experimental value (r, θ) in the crank task (clockwise). In FIGS. 22 and 23, the dotted lines represent values based on the experiment and the solid line is obtained by the multiple regression analysis.

As is found from FIG. 23, both of the curves w1 and w2 obtained by the multiple regression analysis are approximate to the principal component scores obtained by the multivariate analysis using the measurement values, and it was found that they have high correlation. Therefore, a myoelectric potential signal can be synthesized to generate a motion without measuring counterclockwise myoelectric potential.

As stated above, when a principal component analysis is performed for various motion contents beforehand and principal components thereof are specified, then the coordinate conversion unit 131 can convert a motion command in rectangular coordinate system into polar coordinates, which further is converted, including accessary information as needed, by the principal component score conversion unit 132 into principal component scores substantially uniquely (having high correlation) (Steps S101 to S103 of FIG. 15).

Subsequently, the principal component processing unit 141 converts the principal component scores into principal components, and the output conversion unit 142 calculates an antagonistic muscle ratio and a muscle activity for each antagonistic muscle pair. Then, the muscle action command generation unit 143 generates a potential signal to be applied to an agonist muscle and an antagonist muscle based on the obtained antagonistic muscle ratio and muscle activity for each antagonistic muscle pair. When the control target 160 is a human, the potential signal is output to corresponding electrodes 151. The antagonistic muscle ratio and the muscle activity used for muscle coordination can reduce the number of control signals.

Note here that the present invention can use the following embodiments.

(1) When the control target 160 is a musculoskeletal robot provided with artificial muscle arms, e.g., an upper limb musculoskeletal robot, a mechanism is required to convert a target hand motion into an artificial muscle motion command similarly to a human body. In the case where a system includes a master side provided with an electromyograph detecting a human body motion and a controller generating a muscle action command as stated above and a robot on a slave device side that moves in accordance with an output signal from the master side (a so-called master-slave system), since a human and a robot have different muscle properties and structures, an antagonistic muscle ratio and muscle activity obtained in real time from a myoelectric potential measurement result of a human have to be converted into an antagonistic muscle ratio and muscle activity of a robot.

Figure 24:
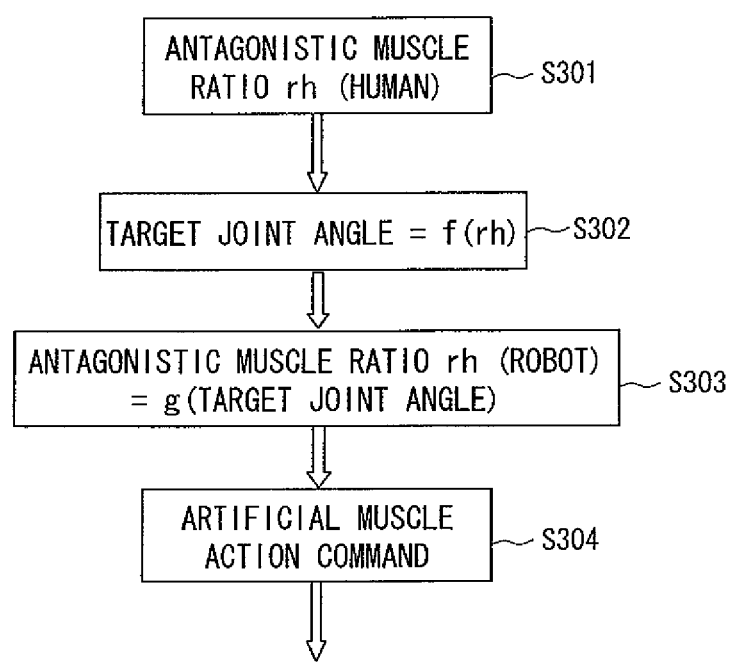
FIG. 24 is a flowchart illustrating exemplary conversion processing of an antagonistic muscle ratio.

FIG. 24 is a flowchart illustrating exemplary conversion processing of an antagonistic muscle ratio. The same goes for muscle activity. Conversion functions f and g may be acquired beforehand based on experimental results, for example. In another method, a relationship between an antagonistic muscle ratio and a hand position may be experimentally found and a principal component vector may be decided so that displacement of the hand position in the radius direction with reference to the shoulder corresponds to the first principal component score and the displacement in the deflection angle direction corresponds to the first principal component score, thus converting an antagonistic muscle ratio of the robot.

This flowchart of FIG. 24 is executed at the stage of Step S105 of FIG. 15, for example. Firstly, at Step S301, an antagonistic muscle ratio ($r_h$) (human) (herein $r_h$ corresponds to the aforementioned $r_{tp}$) is generated. Next, at Step S302, a target joint angle=f($r_h$) is set. Further at Step S303 conversion of antagonistic muscle ratio $r_h$ (robot)=g(target joint angle) is performed. Then, instead of Step S106 of FIG. 15, at Step S304, an artificial muscle action command is output. The artificial muscle action command is output as a driving signal dealing with artificial muscle arms (actuators) of a robot. In this way, the present invention is applicable to the master-slave system.

Figure 25A:
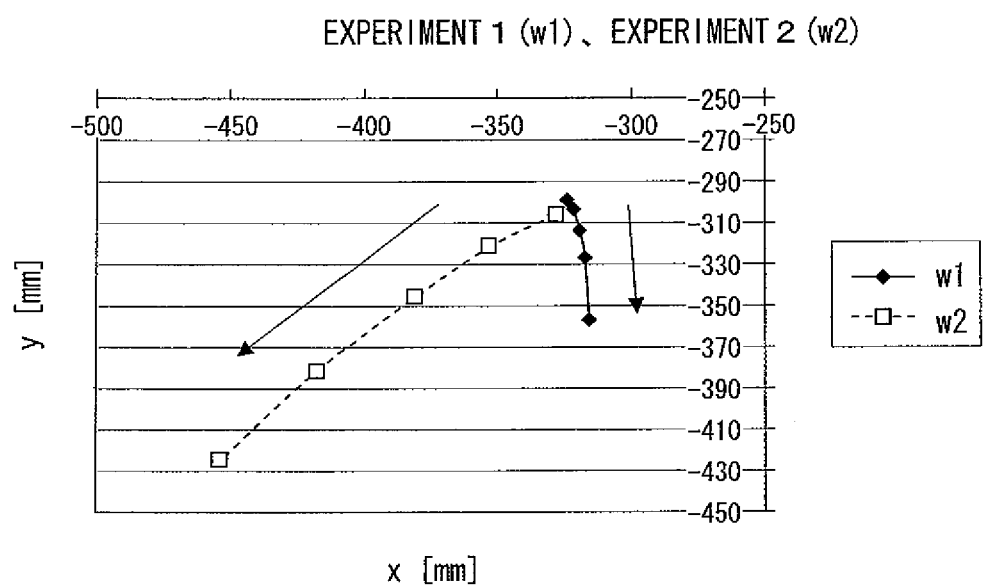
FIGS. 25A and 25B are diagrams to describe driving of an artificial muscle arm, where
Figure 25B:
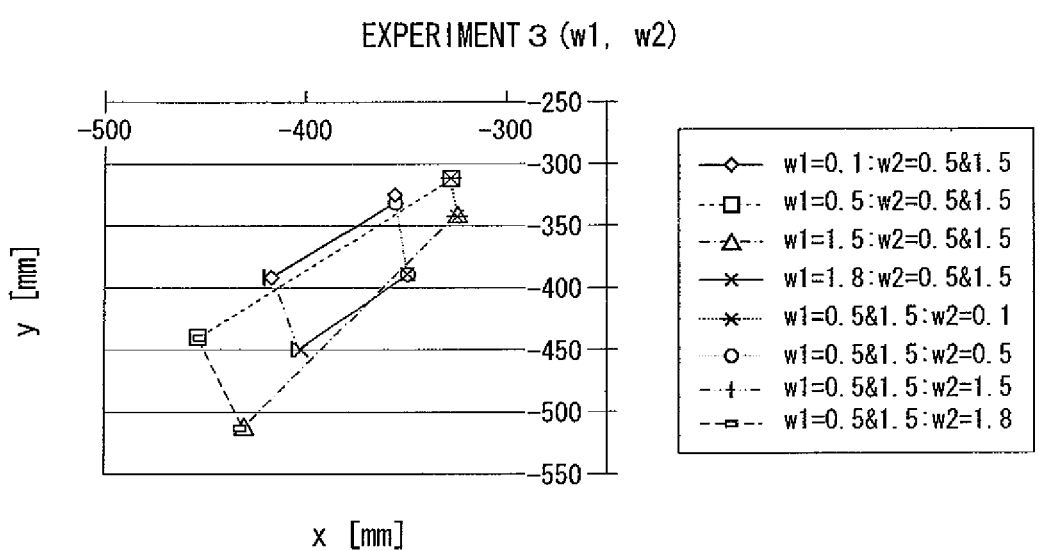

FIGS. 25A and 25B are diagrams to describe driving of an artificial muscle arm. In the case of a robot having a musculoskeletal structure similar to that of a human, a principal component vector to be used for a human may be applied to an artificial muscle arm thereof, whereby a motion command (w1, w2) of a human can be directly used to manipulate the artificial muscle arm. FIG. 25A-FIG. 26B illustrate experimental results where a principal component vector to be used for a human is embedded into a robot having a musculoskeletal structure similar to that of a human, a control command for artificial muscle is calculated, and thereafter the artificial muscle arm is driven.

FIGS. 25A and 25B illustrate the case where principal component scores w1, w2 was given discretely, a control command for artificial muscle was calculated, and thereafter the artificial muscle arm was driven. Experiment 1 (w1) of FIG. 25A was obtained by plotting the hand positions in that case, where the arrows of the graph represents the direction where the principal component score w1 increases discretely. Similarly, Experiment 2 (w2) was obtained by plotting the hand positions when the principal component score w2 was increased discretely.

In FIG. 25B, experiment 3 (w1, w2) shows the result when w1 and w2 are simultaneously changed. According to FIG. 25B, it was found that appropriately given (w1, w2) allows a hand position to be aligned at any position (within a movable range) in a horizontal plane. The artificial muscle arm side may include a controller similar to a human, whereby the artificial muscle arm can be manipulated by directly using the motion command (w1, w2) for a human.

(2) In the present embodiment, rectangular coordinates are used for a motion command set at Step S101 of FIG. 15. Motion information to specify a motion, however, is not limited to this. For instance, a walking motion may use other types of information such as a stride and a cycle as long as the information can specify the motion. In such an embodiment, instead of Steps S101 to S103 of FIG. 15, a method represented by the following Expressions 9 and 10 can be used.

EXPRESSION (9)

SERIES EXPANSION OF PRINCIPAL COMPONENT SCORE MOTION $$\begin{cases} w_1(t) = a_0 + a_1\cos\frac{2\pi}{T}t + a_2\sin\frac{2\pi}{T}t + a_3\cos\frac{4\pi}{T}t + a_4\sin\frac{4\pi}{T}t \\ w_2(t) = b_0 + b_1\cos\frac{2\pi}{T}t + b_2\sin\frac{2\pi}{T}t + b_3\cos\frac{4\pi}{T}t + b_4\sin\frac{4\pi}{T}t \end{cases}$$

MOTION OF $w1$, $w2$ CAN BE EXPRESSED WITH SERIES OF GAIT CYCLE $T$ AND HALF CYCLE $T/2$ $$\begin{cases} w_1(t) + w_1(t+T/2) = 2a_0 + 2a_3\cos\frac{4\pi}{T}t + 2a_4\sin\frac{4\pi}{T}t \\ w_1(t) - w_1(t+T/2) = 2a_1\cos\frac{2\pi}{T}t + 2a_2\sin\frac{2\pi}{T}t \end{cases}$$

$$\begin{cases} w_2(t) + w_2(t+T/2) = 2b_0 + 2b_3\cos\frac{4\pi}{T}t + 2b_4\sin\frac{4\pi}{T}t \\ w_2(t) - w_2(t+T/2) = 2b_1\cos\frac{2\pi}{T}t + 2b_2\sin\frac{2\pi}{T}t \end{cases}$$

Expression 9 represents a feature of the principal component score motion during a walking motion in the form of series expansion. Expression 10 represents the feature using a certain property of w1 and w2 letting that the principal component scores w1 and w2 can be described with a series expansion expression including cycles T and T/2 only. The certain property is that the phase of w1 and w2 is shifted by a half cycle and their sum and difference were found, and then a waveform like a sine wave and a waveform like a cosine wave (waveforms approximate to a sine wave and a cosine wave) is obtained. Then, the cycle will be T/2 of the gait cycle T in the case of finding a sum, and will be T in the case of finding a difference.

The expression form for w1 and w2 to satisfy this property can be obtained by inverse operation, whereby the expression for series expansion of w1(t) and w2(t) as in Expression 9 can be obtained. Herein, variables in the expression are as follows: w1: a first principal component score; w2: a second principal component score; T: one gait cycle; a1, a2, a3, a4: coefficients of series expansion for the first principal component score w1; and b1, b2, b3, b4: coefficients of series expansion for the second principal component score w2.

Figure 26A:
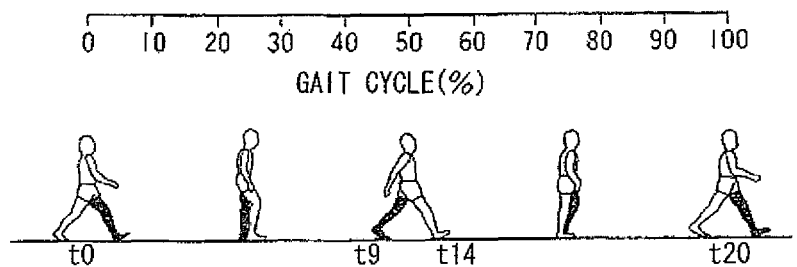
FIGS. 26A-26C are diagrams illustrating an approximation result in series expansion, where
Figure 26B:
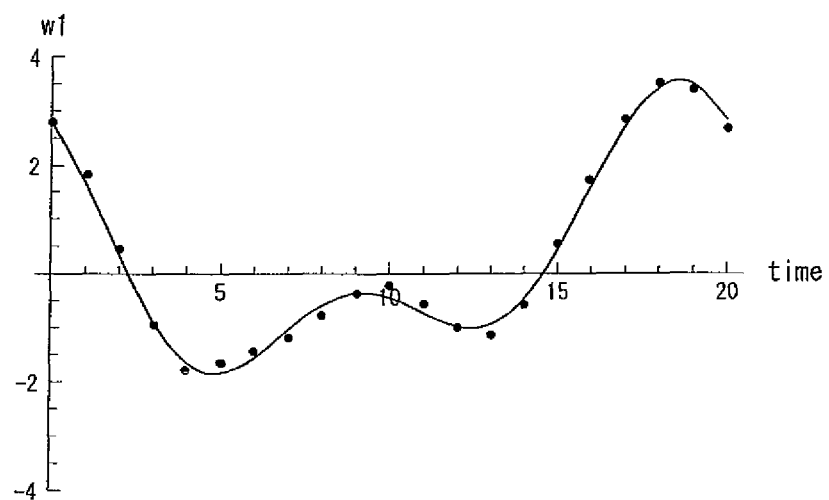
Figure 26C:
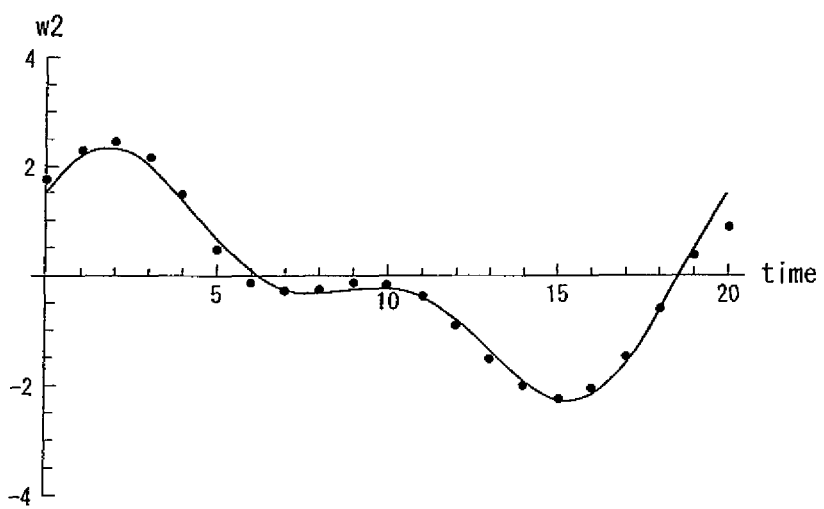

FIGS. 26A-26C are diagrams illustrating an approximation result in series expansion, where FIG. 26A is a diagram of a breakdown of walking (3 km/h) and FIGS. 26B, 26C illustrate principal components w1 and w2 at that time. In FIGS. 26B, 26C, each point represents a principal component score obtained from the measurement result and the solid lines represent an approximate result in this series expansion. It was confirmed that both of the lines are closely analogous.

Expression 10 is the Duffing equation to represent a feature of the principal component score motion during walking motion.

EXPRESSION (10)

BASIC EQUATION OF PRINCIPAL COMPONENT SCORE MOTION $$\begin{cases} \dfrac{d^2 w_1(t)}{dt^2} + c_1 \dfrac{dw_1(t)}{dt} + k_1 w_1^3(t) = A_1 \cos\dfrac{4\pi}{T} t + c_1 z_1 \\ \dfrac{d^2 w_2(t)}{dt^2} + c_2 \dfrac{dw_2(t)}{dt} - k_2 w_2^3(t) = A_2 \sin\dfrac{4\pi}{T} t + c_2 z_2 \end{cases}$$

STATE EQUATION OF PRINCIPAL COMPONENT SCORE MOTION $$v(t) = \begin{pmatrix} w_1(t) \\ \dot{w}_1(t) \\ w_2(t) \\ \dot{w}_2(t) \end{pmatrix}, \quad w(t) = \begin{pmatrix} w_1(t) \\ w_2(t) \end{pmatrix}$$

$$\dot{v}(t) = g(v(t), u(t)) = g0(v(t)) + Bu(t) = A(v(t)) + Bu(t)$$

$$w(t) = \varphi(v(t)) = Cv(t)$$

To explain a walking phenomenon by a human, long time researches in the physiology field shows that a mechanism generating a walking pattern called CPG (Central Pattern Generator) resides at a lower central. Then, researches have been carried out to explain the behavior of such a pattern generator using a nonlinear oscillator. To define the oscillator leads to the definition of a dynamics field representing the behavior of a motion command. On the other hand, in the field of brain science as well, attempt has been made to explain such a phenomenon by assuming a dynamics field in a brain. In this case, a dynamic field to govern a principal component score motion that is the motion command itself has to be found, and to this end, the Duffing equation is used. This equation is a general model applied to various engineering fields. The phase of the solution obtained from the approximation using this equation is shifted by a half cycle, and their sum and difference are found, whereby waveforms like a sine wave and a cosine wave are shown, thus satisfying the phenomenon that is a motivation for the series expansion method illustrated in Expression 9. Although it is difficult to decide parameters for the Duffing equation with an external force applied thereto, various walking motions can be explained with this expression. That is, once parameter can be decided, various walking motions can be described. Herein, the parameters in this expression are as follows when the principal component score motion is represented as a mechanical model: c: viscosity coefficient; k: elasticity coefficient; A: amplitude of cyclic external force (e.g., barycentric motion); T: gait cycle and z: stationary external force (e.g., a speed command from an upper central). Since variables A and z influences more greatly than other parameters in the Duffing equation, such variables A and z, so-called a stride and a gait cycle are appropriately controlled and set, whereby a required motion can be described.

Figure 27A:
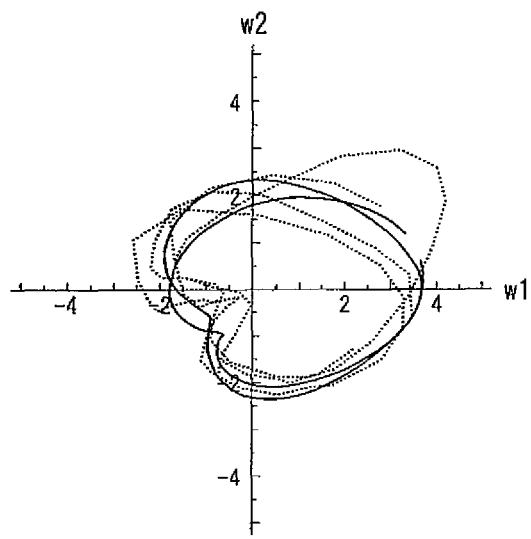
FIGS. 27A-27C are diagrams illustrating an approximation result using the Duffing equation, where
Figure 27B:
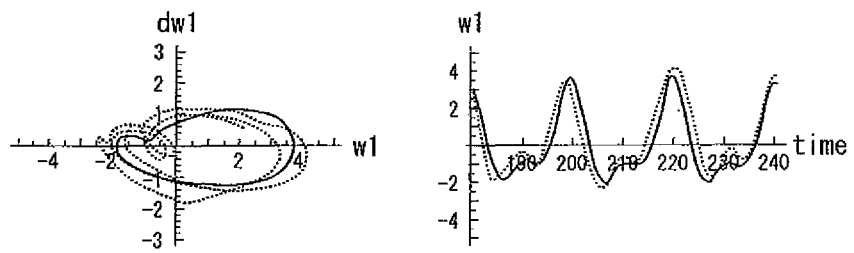
Figure 27C:
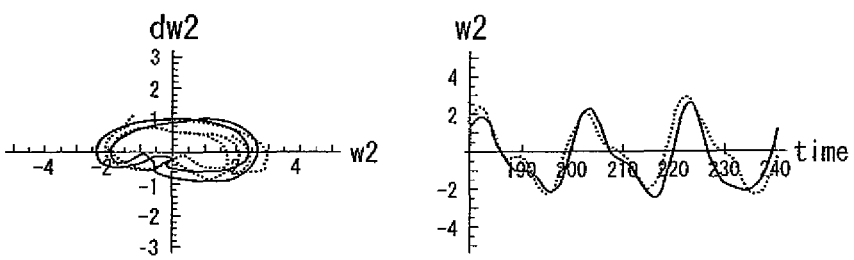

FIGS. 27A-27C are diagrams illustrating the approximation result using the Duffing equation, where FIG. 27A is a diagram of a breakdown of walking (3 km/h), FIG. 27B illustrates information on the principal component w1 at that time and FIG. 27C illustrates information on the principal component w2 at that time. In FIGS. 27B, 27C, the dotted lines represent a principal component score obtained from the measurement result and the solid lines represent an approximate result using the Duffing equation. It was confirmed that both of the lines are closely analogous.

The principal component score for a walking speed different from 3 km/h of FIG. 27, e.g., 4 km/h also can be calculated by changing the parameters in the Duffing equation. In this case also, the approximation was confirmed between the principal component scores obtained from the result of the actual measurement and the principal component scores at 4 km/h estimated by setting the parameter z contributing to the speed in the Duffing equation.

(3) In the present embodiment, two-dimensional motion is described. The present invention, however, is applicable to a one-dimensional motion on an axis as well as a three-dimensional motion as stated above. For instance, in the case of a three-dimensional motion, conversion may be performed from rectangular coordinates to three-dimensional polar coordinates (r, θ, φ) (φ: elevation angle), and the respective polar coordinates may be substituted with principal components in number decided depending on the cumulative contribution, whereby a three-dimensional motion also can be processed similarly to the above.

As stated above, a muscle synergy analysis method according to the present invention preferably includes the steps of: detecting a myoelectric signal generated at each muscle of an antagonistic muscle pair group of a subject; calculating, as time-series data, an antagonistic muscle ratio of an antagonistic muscle pair at a myoelectric signal level from a myoelectric signal detected during a predetermined motion by the subject; and conducting multivariate analysis using the antagonistic muscle ratio at each time of the time-series data as a variable to calculate a principal component including at least a first principal component having high contribution to correlation. With this configuration, instead of conducting a multivariate analysis (in this case, a principal component analysis) to a myoelectric potential matrix of the muscles, the idea of an antagonistic muscle ratio is introduced with consideration given to muscle coordination in the motion, and then a principal component analysis is conducted to this idea. Thereby the types of variables in number can be reduced, thus facilitating and speeding up the processing and so enabling real-time processing. Further, complicated and difficult processing of identifying parameters of various parts of a body is not required, and accordingly the processing can be simplified. When the types of variables after the principal component analysis is up to the third principal component, display can be advantageously performed in a three-dimensional coordinate system. Further, the use of antagonistic muscle ratios allows a different principal component analysis result to be obtained for each type of the motion, and therefore the number and scores of principal components suitable for a motion can be obtained.

Preferably the muscle synergy analysis method according to the present invention further includes the steps of: setting a principal component obtained on a basis of an antagonistic muscle ratio of the subject as a reference principal component, and calculating a difference between a principal component obtained on a basis of a antagonistic muscle ratio of the subject calculated by a new examination and the reference principal component; and displaying the calculated difference on a first display unit. With this configuration, when the subject is the same person, a comparison with the reference motion state acquired beforehand as his/her own reference is shown as the difference, and therefore advice bringing the state to a reference state can be correctly obtained.

Preferably the muscle synergy analysis method according to the present invention further includes the steps of: adding levels of a myoelectric signal of the antagonistic muscle pair from a myoelectric signal detected during a motion by the subject to calculate time-series data of muscle activity; and conducting multivariate analysis using the muscle activity at each time of the time-series data as a variable to calculate a principal component including at least a first principal component having high contribution to correlation. With this configuration, a new concept of, preferably, muscle activity is introduced for an antagonistic muscle pair in addition to the multivariate analysis to an antagonistic muscle ratio, and multivariate analysis is conducted to this new component. The use of the concept of the muscle activity together with the antagonistic muscle ratio enables more precise estimation and evaluation for a motion.

Preferably the muscle synergy analysis method according to the present invention further includes the steps of: setting a principal component obtained on a basis of muscle activity of the subject as a reference principal component, and calculating a difference between a principal component obtained on a basis of muscle activity of the subject calculated by a new examination and the reference principal component; and displaying the calculated difference on a second display unit. With this configuration, a comparison with the reference motion state acquired beforehand as his/her own reference is shown as the difference, and therefore advice bringing the state to a reference state can be correctly obtained.

A muscle synergy analyzer according to the present invention includes: a detector that detects a myoelectric signal generated at each muscle of an antagonistic muscle pair group of a subject; antagonistic muscle ratio calculation means that calculates, as time-series data, an antagonistic muscle ratio of an antagonistic muscle pair at a myoelectric signal level from a myoelectric signal detected by the detector during a predetermined motion by the subject; and first principal component analysis means that conducts multivariate analysis using the antagonistic muscle ratio at each time of the time-series data as a variable to calculate a principal component including at least a first principal component having high contribution to correlation. This aspect of the invention has an effect similar to that of the muscle synergy analysis method.

Preferably the muscle synergy analyzer according to the present invention further includes: first difference calculation means that calculates a difference between a principal component for a first subject and a principal component for a second subject; and first display control means that displays the difference calculated by the first difference calculation means on a first display unit. With this configuration, since the difference between the first subject and the second subject is specifically displayed, comparison therebetween can be made precise and easy. For instance, when persons with a similar physique perform the same motion, a mutual difference can be known specifically.

Preferably in the muscle synergy analyzer according to the present invention, the first subject and the second subject are a same subject. With this configuration, when the first and the second subjects are the same person, comparison with the reference motion state acquired beforehand as his/her own reference is shown as the difference, and therefore advice bringing the state to a reference state can be correctly obtained.

Preferably in the muscle synergy analyzer according to the present invention, a cumulative value of contribution of the principal components exceeds a first threshold. With this configuration, since the types of the principal components obtained by the multivariate analysis have the cumulative contribution exceeding the first threshold, a reliable analysis result can be obtained.

Preferably the muscle synergy analyzer according to the present invention further includes: muscle activity calculation means that adds levels of a myoelectric signal of the antagonistic muscle pair from a myoelectric signal detected by the detector during a motion by the subject to calculate time-series data of muscle activity; and second principal component analysis means that conducts multivariate analysis using the muscle activity at each time of the time-series data as a variable to calculate a principal component including at least a first principal component having high contribution to correlation. With this configuration, a new concept of, preferably, muscle activity is introduced for an antagonistic muscle pair in addition to the multivariate analysis to an antagonistic muscle ratio, and multivariate analysis is performed to this component. The use of the concept of the muscle activity together with the antagonistic muscle ratio enables more precise estimation and evaluation for a motion.

Preferably the muscle synergy analyzer according to the present invention further includes: second difference calculation means that calculates a difference between a principal component for a first subject and a principal component for a second subject; and second display control means that displays the difference calculated by the second difference calculation means on a second display unit. With this configuration, since the difference between the first subject and the second subject is specifically displayed, comparison therebetween can be made precise and easy. For instance, when persons with a similar physique perform the same motion, a mutual difference can be known specifically.

Preferably in the muscle synergy analyzer according to the present invention, a cumulative value of contribution of the principal components exceeds a second threshold. With this configuration, since the types of the principal components obtained by the multivariate analysis have the cumulative contribution exceeding the first threshold, a reliable analysis result can be obtained.

A muscle synergy interface according to the present invention is configured to let a plurality of muscles perform a predetermined motion. The muscle synergy interface includes: motion command setting means that inputs motion information to specify a motion to be performed by the plurality of antagonistic muscle pair groups; first conversion means that converts the motion information into a principal component information; and second conversion means that converts the principal component information into a potential signal to be applied to each antagonistic muscle pair. This aspect of the invention enables a motion instruction to each antagonistic muscle pair with less principal component information having high correlation. Therefore, the processing can be speeded up and the configuration can be made more compact than conventional ones.

Preferably in the muscle synergy interface according to the present invention, the first conversion means converts positional information on a rectangular coordinate system as the motion information into a polar coordinate system.

Preferably in the muscle synergy interface according to the present invention, the first conversion means converts a motion cycle and a unit motion in one cycle as the motion information into a polar coordinate system. With this configuration, information other than positional information in a rectangular coordinate system can be used, and therefore greater versatility can be obtained depending on the control target.

Preferably in the muscle synergy interface according to the present invention, the first conversion means converts the motion information into two types of principal component information, and the second conversion means converts the obtained principal component information into a potential signal to be applied to each antagonistic muscle pair. With this configuration, the principal component information can be two types having high contribution and these two types of principal component information can be converted into at least a potential signal to be applied to each antagonistic muscle pair, and therefore a motion having high correlation is enabled.

Preferably in the muscle synergy interface according to the present invention, the first conversion means converts a distance and a rotation angle between a motion base part and a motion end part that are made up of at least the plurality of antagonistic muscle pair groups into two types of principal component information, and the second conversion means converts the obtained two types of principal component information into a potential signal to be applied to each antagonistic muscle pair. With this configuration, two types of principal component information can be substituted with a distance and a rotation angle.

Preferably in the muscle synergy interface according to the present invention, the first conversion means calculates an eigenvalue in accordance with constraints during execution of the motion. With this configuration, the eigenvalue can be set in accordance with accessary information such as a speed of a motion, acceleration, dynamics interference and constraints to a motion to a forward end of the motion, and therefore a principal component score can be set in accordance with such accessary information.

Preferably in the muscle synergy interface according to the present invention, the second conversion means converts the principal component information into an antagonistic muscle ratio and activity. With this configuration, the present invention is applicable to a control target such as a human or a robot having artificial muscles simulating a human.

REFERENCE SIGNS LIST

1 Muscle synergy analyzer
10 Electromyograph (detector)
20 Signal processing unit
201 Measurement processing unit
202 Antagonistic muscle ratio calculation unit (antagonistic muscle ratio calculation means)
203 First principal component analysis unit (first principal component analysis means)
204 First difference calculation unit (first difference calculation means)
205 Display control unit (first display control means, second display control means)
206 Muscle activity calculation unit (muscle activity calculation means)
207 Second principal component analysis unit (second principal component analysis means)
208 Second difference calculation unit (twenty-first difference calculation means)
24 Monitor (first display unit, second display unit)
100 Muscle synergy interface
110 Motion comment setting unit
120 Controller
130 First conversion unit
131 Coordinate conversion unit
132 Principal component score conversion unit
140 Second conversion unit
141 Principal component processing unit
142 Output conversion unit
143 Muscle action command generation unit
150 Output unit
151 Electrode
160 Control target

The invention claimed is:

1. A muscle synergy analysis method, comprising:
  detecting in a time-divisional manner, at each one muscle of an antagonistic muscle pair group of a first human using a first electrode attached to a skin surface overlying said one muscle, a first myoelectric signal generated at said one muscle during a predetermined motion;
  storing said myolelectric signal into a RAM as reference data;
  detecting in said time-divisional manner, at each one muscle of an antagonistic muscle pair group of a compared human using a second electrode attached to a skin surface overlying said one muscle of said compared human, a second myoelectric signal generated at said one muscle of said compared human during a comparison predetermined motion, wherein the compared human is one of either a same person or a different person than the first human;
  storing said second myolelectric signal into said RAM as comparison data;
  evaluating by a microcomputer a difference in an antagonistic muscle ratio between a principal component of a first antagonistic muscle ratio calculated from said reference data and a principal component of a second antagonistic muscle ratio calculated from said comparison data; and
  displaying said evaluated, antagonistic muscle ratio difference at a display monitor; and
  wherein said evaluating comprises:
    reading the reference data from said RAM,
    calculating said first antagonistic muscle ratio as a time series of first antagonistic muscle ratio values from a time series of said reference data corresponding to said first myolelectric signal of said each one muscle of said antagonistic muscle pair of said first human,
    conducting multivariate analysis on said time series of reference data in which a corresponding first antagonistic muscle ratio value from said times series of said first antagonistic muscle ratio values is a variable at a corresponding time of the time-series of said reference data, and calculating the principal component of said first antagonistic muscle ratio to include at least a first principal component having high contribution to a first correlation;
    reading the comparison data from said RAM,
    calculating said second antagonistic muscle ratio as a time series of second antagonistic ratio values from a time series of said comparison data corresponding to said second myolelectric signal of said each one muscle of said antagonistic muscle pair of said compared human, and
    conducting multivariate analysis on said time series of comparison data in which a corresponding second antagonistic muscle ratio value from said times series of said second antagonistic muscle ratio values is a variable at a corresponding time of the time-series of said comparison data, and calculating the principal component of said second antagonistic muscle ratio to include at least a second principal component having high contribution to a second correlation.

2. The muscle synergy analysis method of claim 1, further comprising:
evaluating by the microcomputer a difference in relation to a muscle activity level between a third principal component of a muscle activity level for a reference calculated on a basis of the reference data acquired by said detecting step for said first human and a fourth principal component in relation to a muscle activity level calculated on the basis of the myoelectric signal of the compared human acquired by the detecting step for said compared human, and displaying said difference in relation to said muscle activity level to the display monitor, wherein said evaluating said difference in relation to said muscle activity level comprises:
reading the reference data from said RAM;
calculating time-series data of a muscle activity level which is a sum of levels of the myoelectric signals of the antagonistic muscle pair for the first human;
conducting multivariate analysis in which the muscle activity level is set at each time of the time-series data for the first human as a variable, and
calculating the third principal component in relation to the muscle activity level as the third principal component of the muscle activity level for reference, the third principal component in relation to the muscle activity level including at least a first component which has a high contribution ratio to a third correlation;
reading the comparison data from said RAM;
calculating time-series data of a muscle activity level which is a sum of levels of the myoelectric signals of the antagonistic muscle pair for the compared human;
conducting multivariate analysis in which the muscle activity level is set at each time of the time-series data for the compared human as a variable, and
calculating the fourth principal component in relation to the muscle activity level as the fourth principal component of the muscle activity level for comparison, the fourth principal component in relation to the muscle activity level including at least a second component which has a high contribution ratio to a fourth correlation.

3. A muscle synergy analysis method, comprising:
a reference data acquisition step of detecting, through an electrode attached onto a skin surface of each muscle, in a time-divisional manner, a myoelectric signal generated at each muscle of an antagonistic muscle pair group of a human with a predetermined motion, and storing the myoelectric signal into a RAM as reference data;
a comparison data acquisition step of executing, to a motion of a compared human for comparison, a same step as the reference data acquisition step to acquire a myoielectric signal of the compared human, and storing the myoelectric signal of each muscle of the compared human into said RAM, the compared human being either one of a same person or a different person; and
an evaluation step of calculating a difference in relation to an antagonistic muscle ratio between a principal component of an antagonistic muscle ratio for reference calculated on a basis of the reference data acquired by the reference data acquisition step and a principal component in relation to an antagonistic muscle ratio calculated on a basis of the myoelectric signal of the compared human acquired by the comparison data acquisition step, by a microcomputer, and displaying the difference in relation to the antagonistic muscle ratio by outputting a calculated difference to a monitor;
wherein the evaluating step comprises reading the reference data from the RAM, calculating an antagonistic muscle ratio of levels of myoelectric signals of an antagonistic muscle pair as time-series data, conducting multivariate analysis in which the antagonistic muscle ratio is set as a variable for each time of the time-series data, and calculating the principal component in relation to the antagonistic muscle ratio for reference, the principal component in relation to the antagonistic muscle ratio including at least a first component which has a high contribution ratio to a first correlation; and
wherein the evaluation step further comprises reading the myoelectric signal of each muscle of the compared human from the RAM, and calculating the principal component in relation to the antagonistic muscle ratio on a basis of the myoelectric signal of each muscle of the compared human by a same method as the calculating of the principal component of the antagonistic muscle ratio for reference.

4. The muscle synergy analysis method of claim 3, further comprising:
a second evaluation step of calculating a difference in relation to a muscle activity level between a principal component of a muscle activity level for reference calculated on a basis of the reference data acquired by said reference data acquisition step and, a principal component in relation to a muscle activity level calculated on the basis of the myoelectric signal of the compared human acquired by the comparison data acquisition, by said microcomputer, and displaying said difference in relation to said muscle activity level to the display monitor,
wherein said second evaluation step comprises:
reading the reference data from said RAM;
calculating time-series data of a muscle activity level which is a sum of levels of the myoelectric signals of the antagonistic muscle pair for the first human;
conducting multivariate analysis in which the muscle activity level is set at each time of the time-series data as a variable, and
calculating the principal component in relation to the muscle activity level as the principal component of the muscle activity level for reference, the principal component in relation to the muscle activity level including at least a first component which has a high contribution ratio to a correlation;
reading the comparison data from said RAM;
calculating time-series data of a muscle activity level which is a sum of levels of the myoelectric signals of the antagonistic muscle pair for the compared human;
conducting multivariate analysis in which the muscle activity level is set at each time of the time-series data for the compared human as a variable, and
calculating the principal component in relation to the muscle activity level as the principal component of the muscle activity level for comparison, the principal component in relation to the muscle activity level including at least a second component which has a high contribution ratio to a fourth correlation.

* * * * *